United States Patent [19]

Reichler et al.

[11] Patent Number: 5,725,831
[45] Date of Patent: Mar. 10, 1998

[54] NUCLEIC ACID AMPLIFICATION APPARATUS

[75] Inventors: Allen S. Reichler, Owings Mills, Md.; Peter A. Bourdelle, Glen Rock, Pa.; Raymond F. Cracauer, Plymouth, Minn.

[73] Assignee: Becton Dickinson and Company, Franklin Lakes, N.J.

[21] Appl. No.: 409,805

[22] Filed: Mar. 24, 1995

Related U.S. Application Data

[63] Continuation-in-part of Ser. No. 213,304, Mar. 14, 1994.

[51] Int. Cl.$^6$ ..................... G01N 21/03
[52] U.S. Cl. .................. 422/56; 422/58; 422/61; 422/68.1; 422/102; 422/104; 436/86; 436/94; 436/180; 436/501; 436/508; 435/6; 435/91
[58] Field of Search ................ 422/50, 58, 61, 422/68.1, 73, 56, 82.09, 102, 104; 436/63, 94, 86, 180, 501, 508, 807; 435/6, 91, 172.3, 301

[56] References Cited

U.S. PATENT DOCUMENTS

| | | | |
|---|---|---|---|
| 3,815,790 | 6/1974 | Allen et al. | 222/309 |
| 4,018,652 | 4/1977 | Lanham et al. | 195/103.5 |
| 4,055,394 | 10/1977 | Friedman et al. | 23/253 |
| 4,260,392 | 4/1981 | Lee | 23/230 |
| 4,580,897 | 4/1986 | Nelson et al. | 356/246 |
| 4,596,695 | 6/1986 | Cottingham | 422/58 |
| 4,623,519 | 11/1986 | Cornut et al. | 422/72 |
| 4,673,657 | 6/1987 | Christian | 436/501 |
| 4,714,590 | 12/1987 | Guigan | 422/102 |
| 4,735,502 | 4/1988 | Kaufmann | 356/246 |
| 4,774,192 | 9/1988 | Terminiello et al. | 436/530 |
| 4,775,515 | 10/1988 | Cottingham | 422/73 |
| 4,883,763 | 11/1989 | Holen et al. | 436/45 |
| 4,902,479 | 2/1990 | Bri kus | 422/72 |
| 4,902,624 | 2/1990 | Columbus et al. | 435/316 |

(List continued on next page.)

FOREIGN PATENT DOCUMENTS

| | | |
|---|---|---|
| 1304916 | 7/1992 | Canada . |
| 0246760 | 11/1987 | European Pat. Off. . |
| 0381501 | 8/1990 | European Pat. Off. . |
| 0480497 | 4/1992 | European Pat. Off. . |
| 0057110 | 8/1992 | European Pat. Off. . |
| 0585660 | 3/1994 | European Pat. Off. . |
| 9316801 | 9/1993 | WIPO . |
| 9322058 | 11/1993 | WIPO . |
| 9404929 | 3/1994 | WIPO . |

OTHER PUBLICATIONS

C.A. Burdis et al, "Factors Influencing Evaporation From Sample Cups, and Assessment on Analytical Error", *Clinical Chemistry*, vol. 31, No. 13, pp. 1867 –1977 (1975).

*Primary Examiner*—Harold Y. Pyon
*Attorney, Agent, or Firm*—David W. Highet, Esq.

[57] ABSTRACT

An apparatus for containing a liquid biological sample and for performing a biological process thereon comprises a sample area for receiving the sample, at least one reaction area in fluid communication with the sample area, a pneumatic area in pneumatic communication with the reaction area and the sample area, and a pneumatic port in the pneumatic area for connection of the apparatus to a pneumatic aspiration/dispensing pipette. The pneumatic aspiration/dispensing pipette provides for controlled flow of the liquid biological sample between the sample area and the reaction area. To reduce evaporative loss of the sample from the apparatus, a sample tower is provided in fluid communication with the sample area. A similar tower may be provided at the pneumatic port to reduce evaporative loss through the pneumatic area. A restricted orifice between the sample tower and the sample area holds the liquid sample in place during removal of the sample from the apparatus, counteracting the tendency of the liquid bolus to flow back toward the reaction area due to capillary forces. Also disclosed is a novel sealing arrangement which provides an effective pneumatic seal between the pneumatic port and a pneumatic aspiration/dispensing pipette without requiring the apparatus to include a separate "O" ring or other type of discrete sealing device.

17 Claims, 12 Drawing Sheets

U.S. PATENT DOCUMENTS

| | | | |
|---|---|---|---|
| 4,929,236 | 5/1990 | Sampson | 604/175 |
| 4,965,188 | 10/1990 | Mullis et al. | 435/6 |
| 5,035,996 | 7/1991 | Hartley | 435/6 |
| 5,061,446 | 10/1991 | Guigan | 422/64 |
| 5,110,552 | 5/1992 | Guigan | 422/64 |
| 5,122,284 | 6/1992 | Braynin et al. | 210/782 |
| 5,141,868 | 8/1992 | Shanks et al. | 435/288 |
| 5,147,606 | 9/1992 | Charlton et al. | 422/56 |
| 5,147,609 | 9/1992 | Grenner | 422/38 |
| 5,171,537 | 12/1992 | Wainwright et al. | 422/100 |
| 5,187,084 | 2/1993 | Hallsby | 435/91 |
| 5,188,963 | 2/1993 | Stapleton | 435/299 |
| 5,219,762 | 6/1993 | Katamine et al. | 436/518 |
| 5,229,297 | 7/1993 | Schnipelsky et al. | 436/94 |
| 5,240,844 | 8/1993 | Wie et al. | 435/7.92 |
| 5,256,376 | 10/1993 | Callan et al. | 422/102 |
| 5,302,348 | 4/1994 | Cusack et al. | 422/73 |
| 5,304,487 | 4/1994 | Wilding et al. | 435/291 |
| 5,364,744 | 11/1994 | Buican et al. | 430/321 |
| 5,378,638 | 1/1995 | Deeg et al. | 436/518 |
| 5,422,270 | 6/1995 | Caspi | 435/284 |
| 5,422,271 | 6/1995 | Chen et al. | 435/287 |
| 5,424,220 | 6/1995 | Goerlach-Graw et al. | 436/568 |
| 5,468,453 | 11/1995 | Holt et al. | 422/100 |

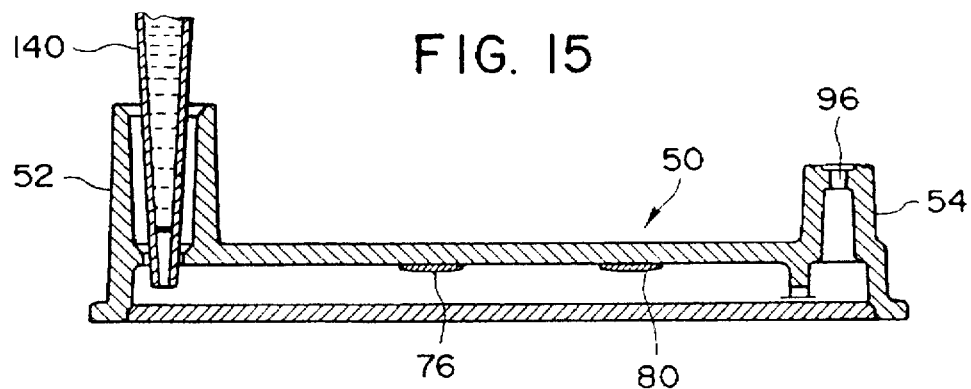
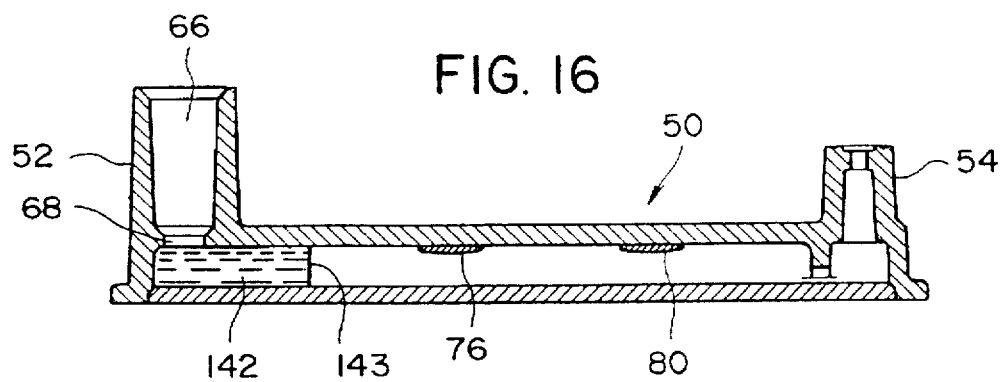
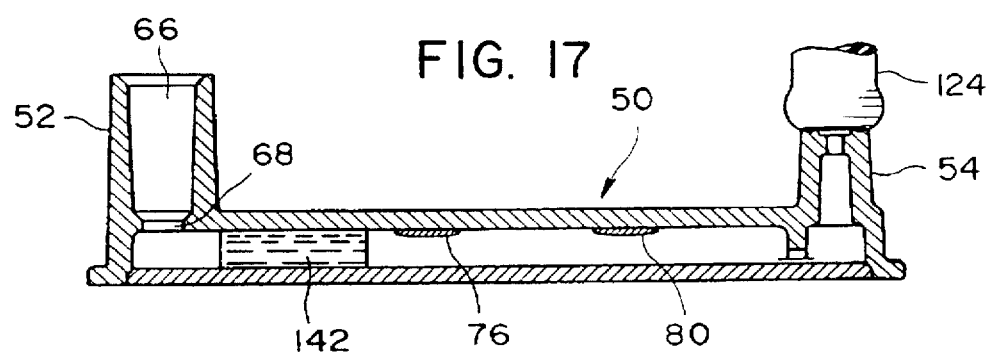
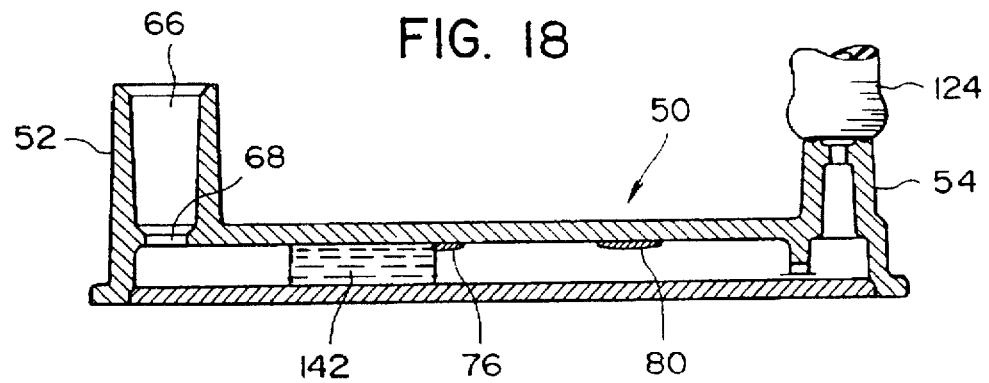

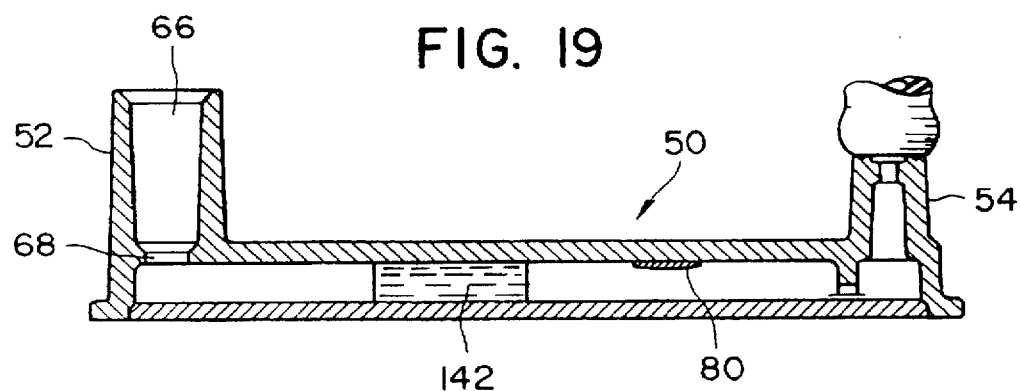
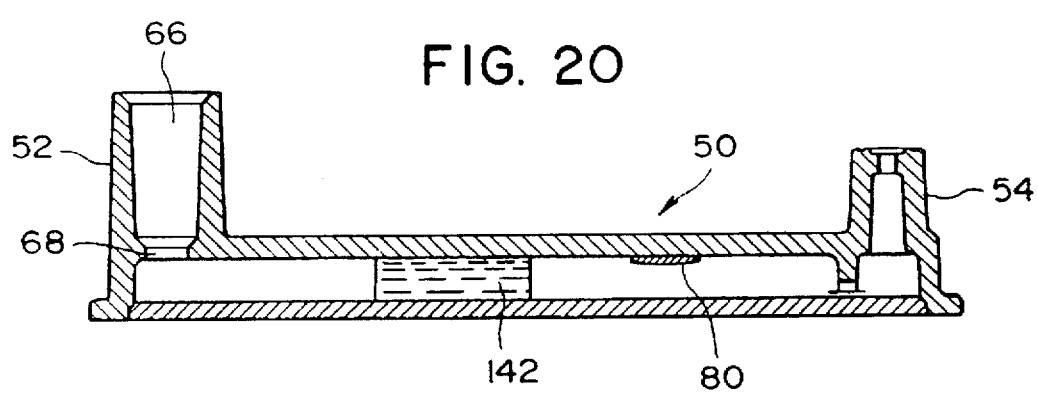
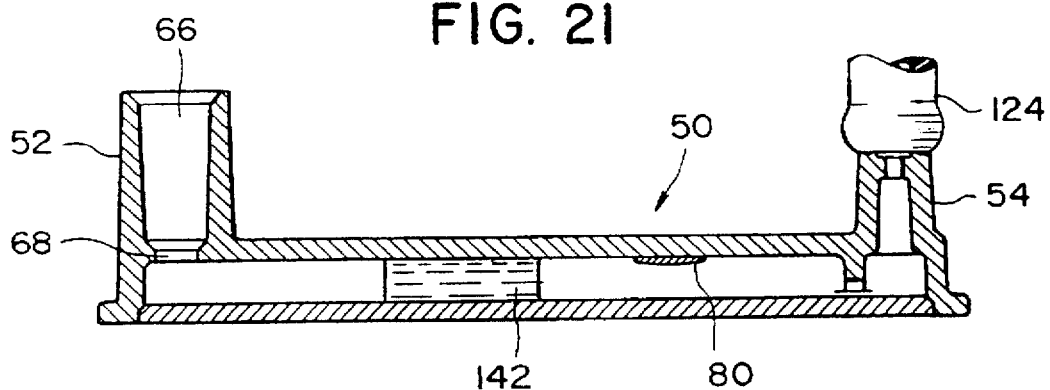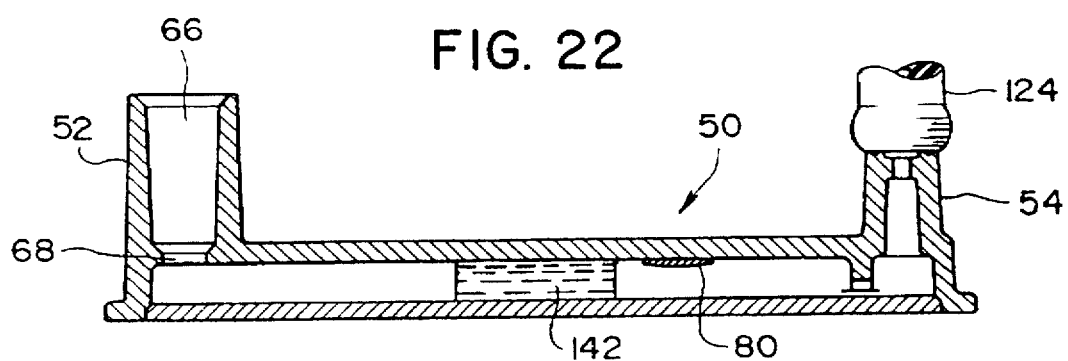

NUCLEIC ACID AMPLIFICATION APPARATUS

This application is a continuation-in-part of a copending U.S. patent application of Hugh V. Cottingham et al, Ser. No. 08/213,304, filed on Mar. 14, 1994 and entitled "Nucleic Acid Amplification Method and Apparatus", the disclosure of which is expressly incorporated herein by reference.

CROSS-REFERENCE TO RELATED APPLICATIONS

Related subject matter is disclosed in a copending patent application of Allen S. Reichler et al, filed on even date herewith and entitled "System for Nucleic Acid Based Diagnostic Assay", Ser. No. 08/409,821, and in a copending U.S. patent application of Michael L. Lamos et al, filed on even date herewith and entitled "Pipette Tip", Ser. No. 08/410,245, both of said applications being expressly incorporated herein by reference.

FIELD OF THE INVENTION

The present invention relates to an apparatus useful for carrying out a biological process such as nucleic acid amplification, and particularly relates to a unitary apparatus or module useful for carrying out a biological process including a decontamination step in which contaminating amplicons are removed or destroyed, and an amplification step in which the number of target nucleic acid segments is increased.

BACKGROUND OF THE INVENTION

Biological processes are often utilized in clinical diagnostics assays. However, the steps of the processes frequently are conducted in different areas of the laboratory and/or in different vessels or containers, thereby necessitating transport of biological samples and reagents and giving rise to increased risk of contamination of other clinical samples.

The risk of contamination is of particular concern when the process includes nucleic acid amplification reactions such as strand displacement amplification (SDA) or polymerase chain reaction (PCR), which are capable of multiplying a single strand of nucleic acid (target nucleic acid) into millions of copies (amplicons). While of tremendous potential utility in the clinical diagnostic laboratory, nucleic acid amplification reactions can, however, easily become contaminated with the amplification products (amplicons) of previous amplification reactions. Such contaminating amplicons can in turn contaminate new samples entering the lab, leading to a false positive indication of the substrate to be detected in the contaminated sample (e.g., an incorrect diagnosis).

The problem of amplicon contamination has led to the development of a number of decontamination techniques. In order to be effective, these decontamination techniques generally require that the decontamination step of the process occur prior to the amplification step, thereby greatly decreasing the possibility that a contaminating amplicon will be recognized as target nucleic acid during the amplification step.

Decontamination reagents and amplification reagents are often not compatible with each other and may require their own reaction conditions. Sometimes, if the reagents for decontamination and amplification are combined, they inactivate each other. Furthermore, performing the decontamination reaction in one container and transferring the decontaminated sample to another container for amplification is not a viable option, as there is a high probability that the sample would become recontaminated during the transfer.

In the aforementioned co-pending patent application of Hugh V. Cottingham et al entitled "Nucleic Acid Amplification Method and Apparatus", Ser. No. 08/213,304, an apparatus is described which reduces or eliminates these problems by allowing decontamination and amplification to be carried out within the confines of a single apparatus or module. In general, the disclosed apparatus includes a sample well for the introduction and removal of a liquid biological sample, at least one reaction chamber in fluid communication with the sample well, a pneumatic chamber in pneumatic communication with the reaction chamber and sample well, and a pneumatic port in the pneumatic chamber for allowing connection of the apparatus to a pneumatic aspiration/dispensing means. Operation of the pneumatic aspiration/dispensing means causes the liquid biological sample to flow between the sample well and the reaction chamber in a controlled manner. In a preferred embodiment, the apparatus is generally elongate in shape, with the sample well and pneumatic port at opposite ends and the reaction chamber therebetween. Reagents necessary for the decontamination and amplification reactions are affixed to separate, discrete locations within the reaction chamber.

In the apparatus described above, liquid flow control means in the form of microchannels are used to control the flow of the liquid biological sample between the sample well and the reaction chamber, and, if more than one reaction chamber is provided, between the reaction chambers themselves. In addition to performing the desired liquid flow control function, the microchannels also reduce evaporation of the liquid biological sample from the apparatus during the decontamination and amplification steps. Given the relatively small quantity of liquid biological sample used (typically about 55 microliters), the relatively high temperatures employed during certain portions of the process (up to 80° C.) and the length of time required to complete the decontamination and amplification reactions (approximately 1 and 2 hours, respectively), evaporation of the sample can be a significant problem. In extreme cases, the extent of evaporation may be such that there is an insufficient amount of liquid biological sample remaining to be recovered and assayed after the decontamination and amplification steps are complete. With the use of properly dimensioned microchannels, however, the problem of evaporative loss can be kept under control.

Unfortunately, despite their advantages, microchannels require rather precise dimensional tolerances and are therefore difficult to fabricate. As disclosed in the aforementioned co-pending patent application of Hugh V. Cottingham et al, flow control between successive reaction chambers is possible without the use of microchannels by causing the liquid biological sample to flow as a single undivided unit (bolus) within the apparatus. However, microchannels are still retained at both ends of the apparatus, in part to reduce evaporative loss through the sample well and pneumatic port. Ideally, it would be desirable to eliminate one or both of these remaining microchannels in order to further simplify the design and fabrication of the apparatus.

Apart from evaporative loss, one of the problems that can occur when the microchannels are eliminated from the apparatus is an uncontrolled flow or movement of the liquid bolus during intervals when the pneumatic aspiration/dispensing means is not operating. This is thought to result, at least in part, from thin streams of liquid which form in the interior corners or edges of the apparatus, and which exert a capillary attraction that pulls the bolus in the direction of the streams. Without the blocking effect of the microchannels, this capillary flow phenomenon can make it difficult to control the position of the bolus within the apparatus. For example, if the microchannel between the sample well and the reaction chamber (or chambers) is eliminated, capillary flow may cause the liquid biological sample to move back to the reaction chamber from the sample well after it has been forced into the sample well by the pneumatic aspiration/dispensing means. This may make it difficult or impossible to recover the sample for assay purposes after the decontamination and amplification steps have been completed.

In the apparatus described in the aforementioned co-pending U.S. patent application of Hugh V. Cottingham et al, a sealing device such as an "O" ring is disposed around the pneumatic port at one end of the apparatus in order to form a pneumatic seal with the pipette of a pneumatic aspiration/dispensing means. Although this arrangement creates an effective seal, the need for a separate "O" ring complicates the design and manufacture of the apparatus and increases its cost. Ideally, it would be desirable to create an effective seal with the pneumatic aspiration/dispensing means without the need for an "O" ring or other separate sealing device, so that all parts of the decontamination and amplification apparatus can be made of the same material.

It is therefore an object of the present invention to provide an apparatus for performing a biological process in which microchannels and similar types of flow control means may be deleted if desired, without giving rise to excessive evaporation of the liquid biological sample during decontamination and amplification processes.

It is another object of the invention to provide an apparatus for performing a biological process in which improved control over the position of a liquid bolus can be obtained without the need for microchannels and similar flow control devices, and in which the problem of capillary flow of the liquid bolus is reduced or eliminated.

It is a further object of the invention to provide an apparatus for performing a biological process in which a separate "O" ring or other discrete sealing devices is not required in order to create an effective seal with a pneumatic aspiration/dispensing means.

It is a still further object of the invention to provide improved methods for performing biological processes, which methods can be carried out using the exemplary apparatus disclosed and claimed herein.

SUMMARY OF THE INVENTION

In accordance with one aspect of the present invention, an apparatus for containing a liquid biological sample and for performing a biological process thereon comprises a sample area for receiving a liquid biological sample, at least one reaction area in fluid communication with the sample area, and a pneumatic area in pneumatic communication with the reaction area and the sample area. The sample area has an orifice for admitting the liquid biological sample into the sample area. A pneumatic port is provided in the pneumatic area for allowing the apparatus to be connected to a pneumatic aspiration/dispensing means, which is effective to cause the liquid biological sample to flow between the sample area and the reaction area. The apparatus also includes a sample tower in fluid communication with the sample area for reducing evaporation of the liquid biological sample from the sample area and the reaction area. The sample tower has a sample port for admitting the liquid biological sample into the apparatus. In a preferred embodiment of the invention, the pneumatic area may include a similar tower for reducing evaporation of the liquid biological sample through the pneumatic area.

In another aspect of the present invention, an apparatus for containing a liquid biological sample and for performing a biological process thereon comprises a sample area for receiving a liquid biological sample, at least one reaction area in fluid communication with the sample area, and a pneumatic area in pneumatic communication with the reaction area and the sample area. A pneumatic port is provided in the pneumatic area for allowing the apparatus to be connected to a pneumatic aspiration/dispensing means, which causes the liquid biological sample to flow between the sample area and the reaction area. The apparatus also includes sample admitting means in fluid communication with the sample area for admitting a liquid biological sample to be introduced into the sample area. A restricted orifice is provided between the sample admitting means and the sample area for providing fluid communication therebetween and for inhibiting capillary flow of the liquid biological sample from the sample area to the reaction area, in order to facilitate removal of the sample from the sample area. The sample admitting means may comprise a sample tower of the type described previously.

In a further aspect of the present invention, an apparatus for containing a liquid biological sample and for performing a biological process thereon comprises a sample area for receiving a liquid biological sample, at least one reaction area in fluid communication with the sample area, and a pneumatic area in pneumatic communication with the reaction area and the sample area. A pneumatic port is provided in the pneumatic area for allowing the apparatus to be connected to a pneumatic aspiration/dispensing means, which causes the liquid biological sample to flow between the sample area and the reaction area. The sample area and the reaction areas are provided in the form of a continuous channel through which the liquid biological sample flows in the form of a liquid bolus. At least one corner of the channel which extends in the direction of liquid flow is rounded to reduce capillary flow of the liquid biological sample. In a preferred embodiment of the invention, the channel has two upper corners which extend in the direction of liquid flow, and both of the upper corners of the channel are rounded to reduce capillary flow of the liquid biological sample.

In a still further aspect of the present invention, a system for performing a biological process comprises an apparatus for containing a liquid biological sample and a pneumatic aspiration/dispensing means for controlling the flow of the sample within the apparatus. The apparatus includes a sample area for receiving the liquid biological sample, at least one reaction area in fluid communication with the sample area, a pneumatic area in pneumatic communication with the reaction area and the sample area, and a pneumatic port in the pneumatic area. The pneumatic aspiration/dispensing means is adapted to be brought into contact with the pneumatic port to cause the liquid biological sample to flow between the sample area and the reaction area. The pneumatic port of the apparatus is encircled by at least one rigid sealing ring and the pneumatic aspiration/dispensing means has a resilient portion which is adapted to be deformed by contact with the sealing ring to create a pneumatic seal around the pneumatic port. In a preferred embodiment of the invention, the pneumatic aspiration/ dispensing means comprises a rigid aspiration/dispensing pipette and the resilient portion comprises a resilient tip affixed to the pipette, with an opening in the resilient tip communicating with the lumen of the pipette and adapted to communicate with the pneumatic port of the apparatus.

The present invention is also directed to methods for performing biological processes, which methods may be carried out using the exemplary apparatus disclosed and claimed herein.

BRIEF DESCRIPTION OF THE DRAWINGS

The various objects, advantages and novel features of the invention will be more readily appreciated from the following detailed description when read in conjunction with the appended drawing figures, in which:

FIGS. 15–31 are a series of side sectional views similar to that of FIG. 7, illustrating the manner in which a liquid biological sample flows from the sample area to the decontamination and amplification zones of the reaction area, and back to the sample area, under the control of the pneumatic aspiration/dispensing means.

Throughout the drawings, like reference numerals will be understood to refer to like parts and components.

DETAILED DESCRIPTION OF THE PREFERRED EMBODIMENTS

As noted above, the present invention provides methods and apparatus for carrying out a biological process. In overview, one embodiment of the present invention provides for an apparatus which includes a sample area and at least one reaction area formed therein. The reaction area is in fluid communication with the sample area. The steps of the biological process may be performed at different sites or zones within the reaction area.

In one embodiment adapted for use with a biological process including a decontamination step and an amplification step, a decontamination zone of the reaction area is in fluid communication with the sample area and an amplification zone of the reaction area is in fluid communication with the decontamination zone. Amplicon decontamination reagents are present in the decontamination zone, and nucleic acid amplification reagents are present in the amplification zone. In use, a liquid biological sample containing nucleic acid is moved from the sample area into the decontamination zone of the reaction area, where liquid sample contacts the decontamination reagents and the amplicons in the sample are degraded. The liquid sample is then moved from the decontamination zone to the amplification zone, where the liquid sample contacts the amplification reagents and amplicons are thus generated in the sample. The liquid sample is then moved from the amplification zone, through the decontamination zone to the sample area, where the sample may be withdrawn. Movement of the sample may be carried out by any suitable pneumatic means, and the sample may be withdrawn by any suitable pipetting means.

Once the sample is withdrawn, the presence of amplicons in the sample can be detected by any suitable means, such as with nucleic acid probes which bind to the amplicons, which probes are labeled with detectable groups (e.g., enzymes, radioisotopes, and so on), all in accordance with known techniques. Alternatively, the apparatus may be configured to allow detection steps to be carried out in situ by the inclusion of additional areas and reagents in the apparatus.

Figure 1:
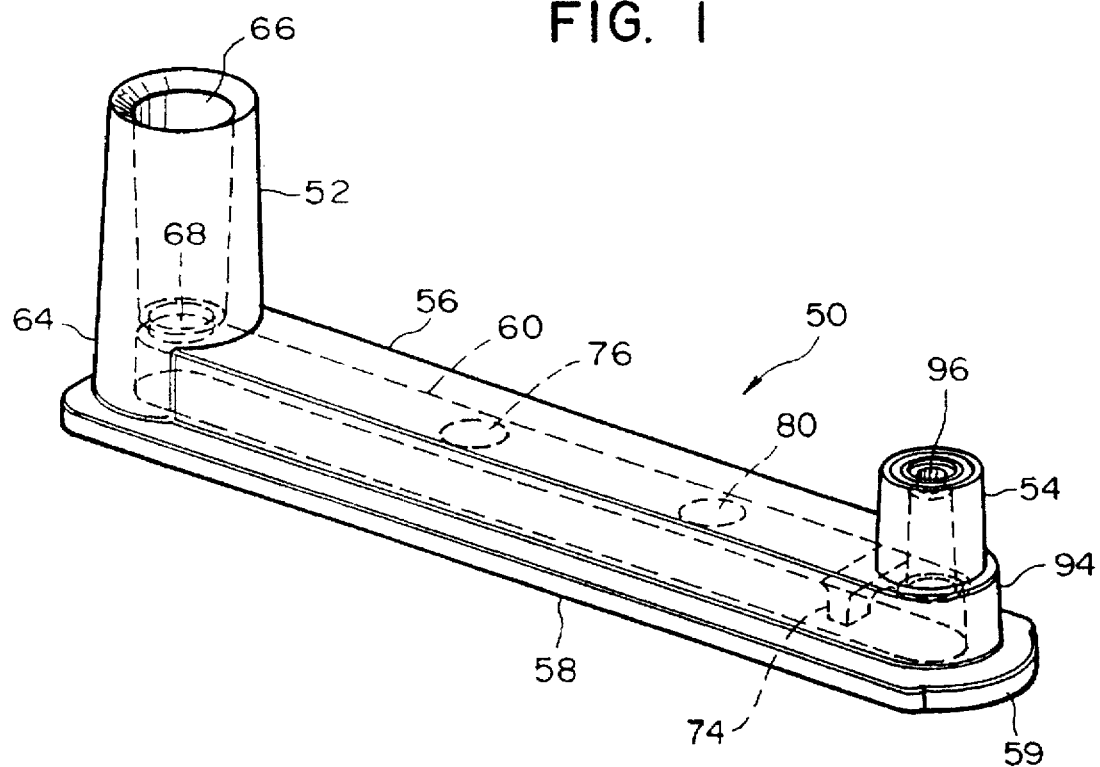
FIG. 1 is a perspective view of one embodiment of an apparatus in accordance with the present invention.
Figure 2:
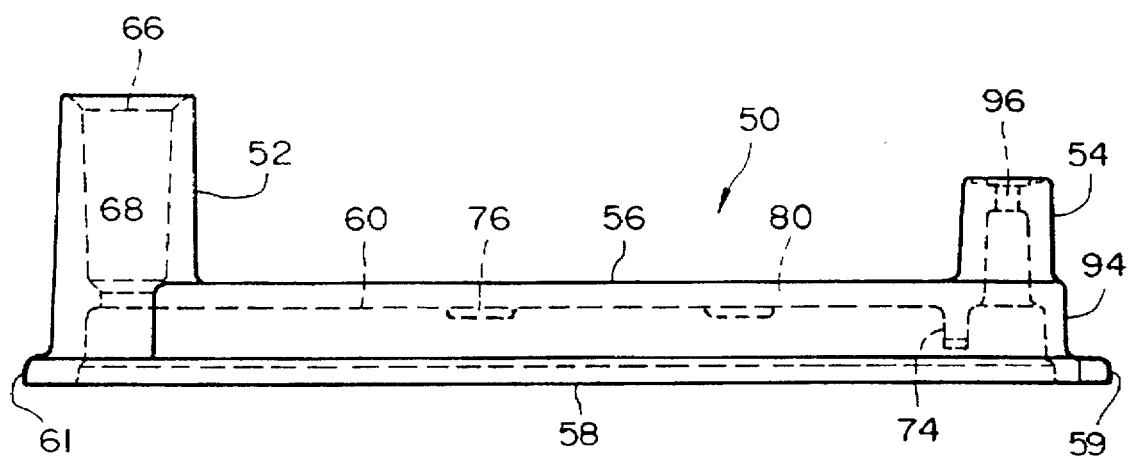
FIG. 2 is a side elevational view of the apparatus shown in FIG. 1.
Figure 3:
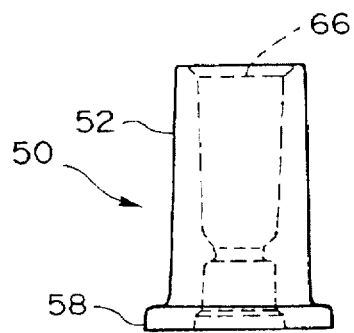
FIG. 3 is a left-hand end view of the apparatus shown in FIG. 2.
Figure 4:
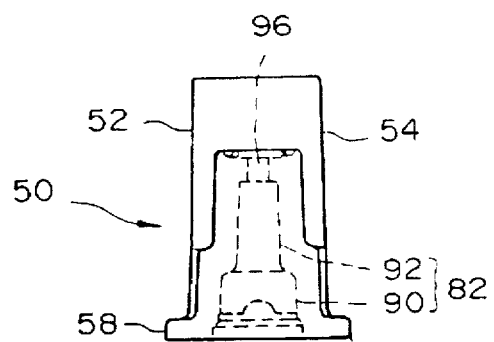
FIG. 4 is a right-hand end view of the apparatus shown in FIG. 2.
Figure 5:
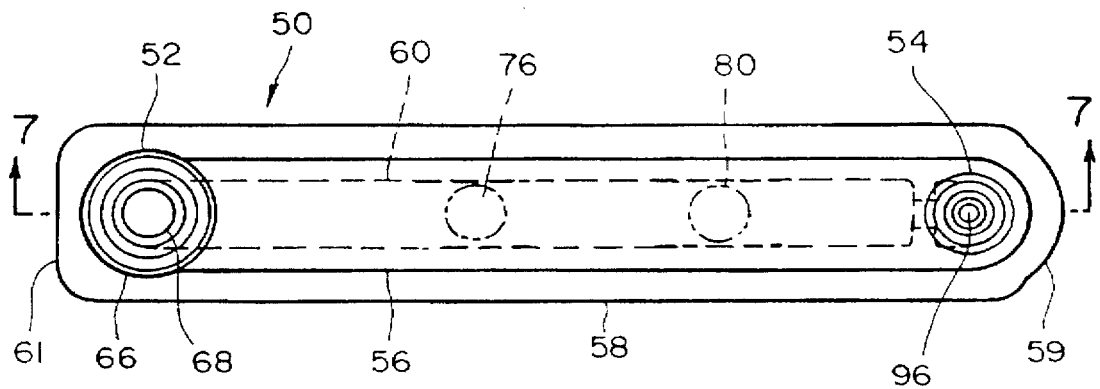
FIG. 5 is a top plan view of the apparatus shown in FIG. 2.
Figure 6:
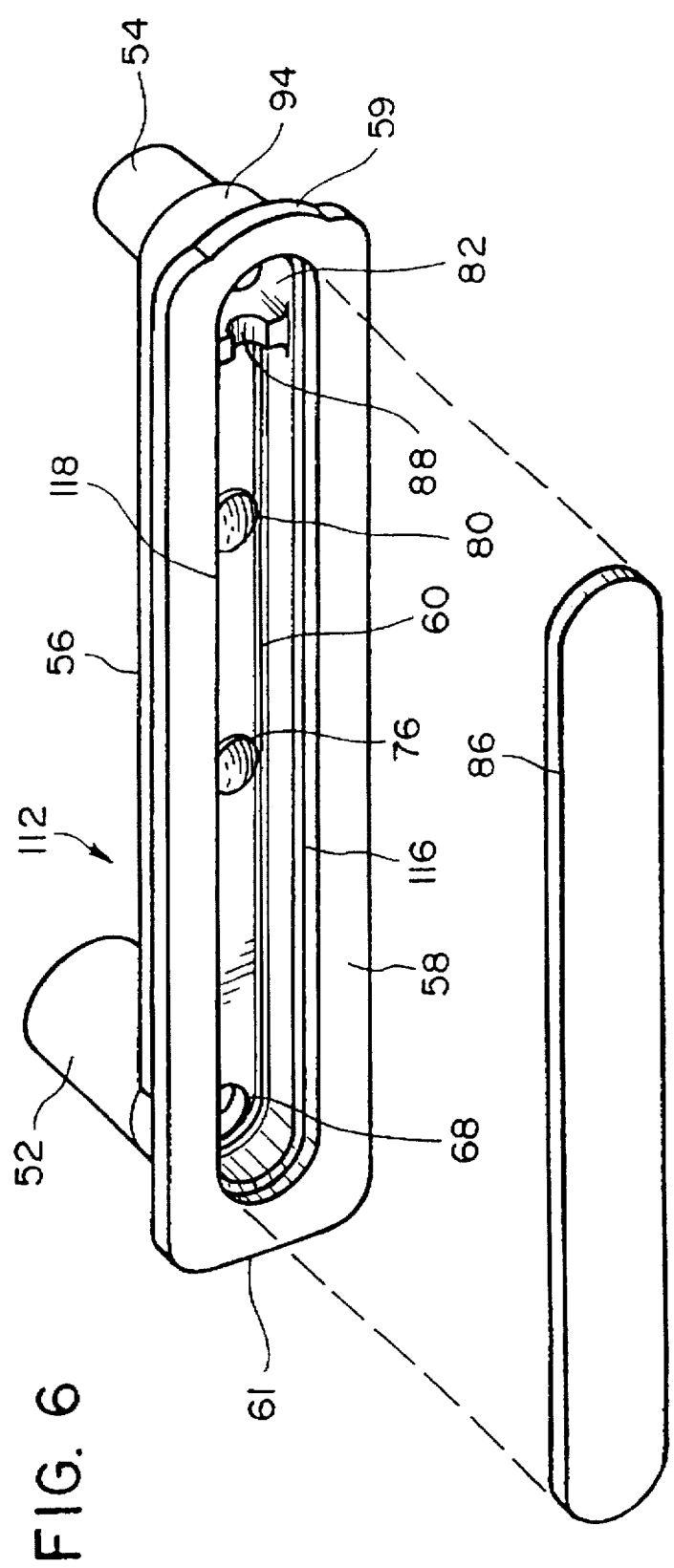
FIG. 6 is an exploded view of the apparatus shown in FIGS. 1–5, illustrating the manner in which the bottom of the apparatus is closed off by an ultrasonically welded plug or insert.

A preferred embodiment of a decontamination and amplification apparatus 50 in accordance with the present invention is illustrated in FIGS. 1–12. With particular reference to the perspective view of FIG. 1, the apparatus 50 is shaped approximately as an elongated rectangular prism, with raised or upstanding towers 52 and 54 at either end, an elongated rectangular body portion 56 extending between the towers, and a base flange 58 which is somewhat wider than the body portion 56. The apparatus has nominal outside dimensions of about 1.669 inches in length, about 0.304 inches in width and about 0.165 inches in height (excluding the towers 52 and 54). The base flange 58 is rounded at its right-hand end 59 with a radius of about 0.150 inch, while the left-hand end 61 of the base flange is straight. This provides the apparatus 50 with an asymmetrical slope or profile in plan, as shown in FIGS. 5 and 6, in order to insure that the apparatus is positioned in a desired orientation within a carrying tray (not shown) during an automated nucleic acid assay. (Reference is made to the aforementioned copending U.S. patent application of Allen S. Reichler et al., entitled "System for Nucleic Acid Based Diagnostic Assay", Ser. No. 08/409,821, for a description of the tray and the automated assay procedure.) The tower 52 is approximately 0.450 inches in height from the bottom surface of the flange 58, and the tower 54 is approximately 0.320 inches in height measured from the same surface. The walls of the apparatus are about 0.040 inch thick. The apparatus 50 is designed to receive a liquid biological sample having a volume of approximately 55 microliters (µL). As will be recognized by those skilled in the art, the dimensions of the apparatus 50 need not be specifically as set forth above, and may be varied substantially depending upon the desired sample capacity and other factors. However, a general guideline for variance of the dimensions is to maintain approximately the same ratios between the dimensions as are represented by the dimensions specified above.

Figure 7:
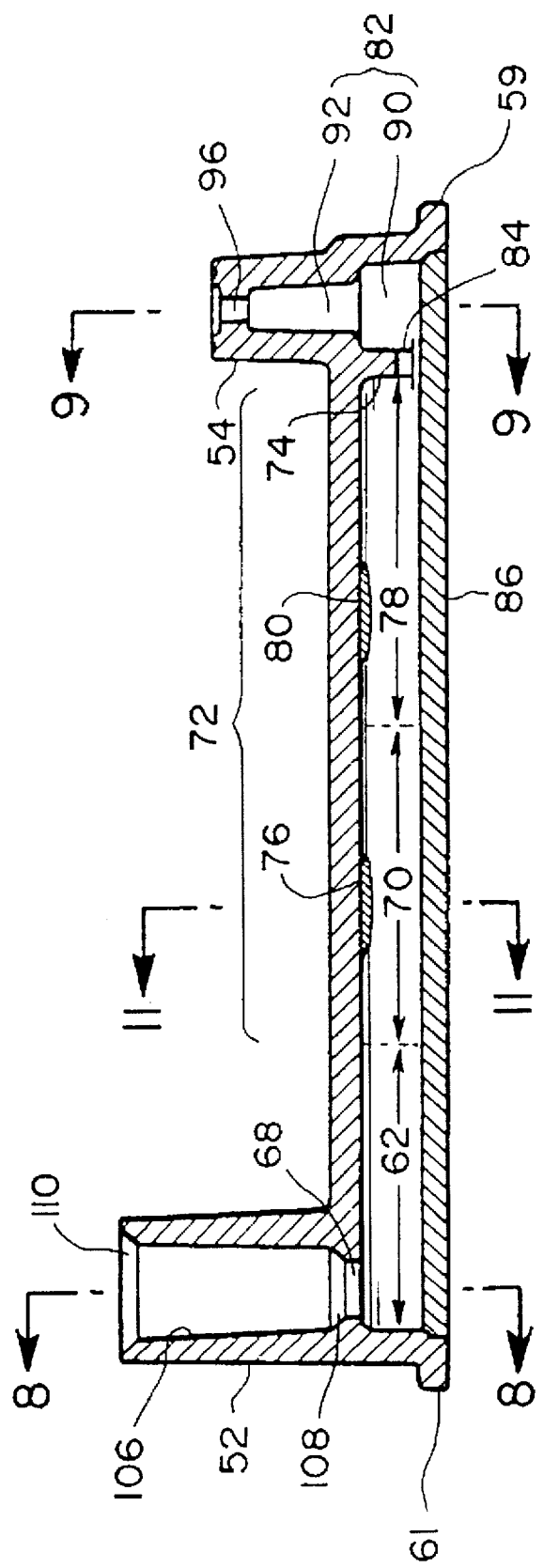
FIG. 7 is a sectional view taken along the line 7—7 in FIG. 5, illustrating the internal configuration of the apparatus.
Figure 8:
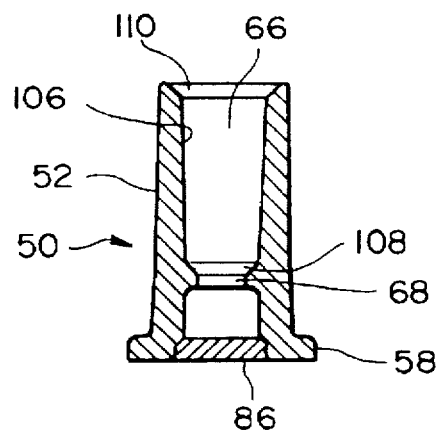
FIG. 8 is a sectional view taken along the line 8—8 in FIG. 7, illustrating the details of the sample area.
Figure 11:
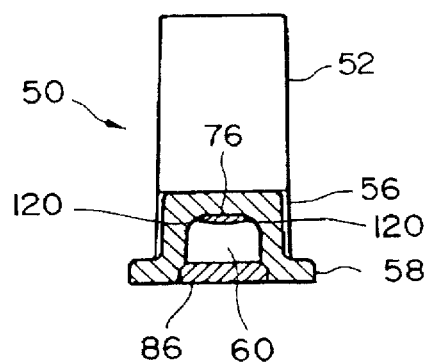
FIG. 11 is a sectional view taken along the line 11—11 in FIG. 7, illustrating the cross-sectional shape of the reaction area of the apparatus.

As can be seen most clearly in FIG. 7, the elongated rectangular body portion 56 of the apparatus 50 contains an internal channel 60 which defines a number of areas or zones for containing the liquid biological sample (not shown) and for carrying out the desired biological process on the sample. In the preferred embodiment, the dimensions and material of the apparatus 50 are chosen such that the liquid biological sample moves as a single undivided unit or bolus through the various areas or zones of the channel 60 under the control of externally applied pneumatic aspiration or dispensing, without the need for barriers or partitions between the areas or zones. This can be achieved by appropriately choosing the dimensions of the channel 60 and by forming the apparatus 50 from a non-wettable material (such as polypropylene) which maintains a contact angle of about greater than or equal to 90° between the surfaces of the apparatus and the liquid sample. In the illustrated embodiment, the channel 60 is generally rectangular in cross-section, as illustrated in FIG. 11, with a height of approximately 0.085 inches and a width of approximately 0.125 inches. The left-most region 62 of the channel 60 in FIG. 7 serves as a sample area for the introduction and withdrawal of a liquid biological sample. The sample area has a length of approximately 0.4 inch within the channel 60 and a volume of approximately 65 µL. One end of the sample area 62 is rounded, corresponding to the rounded left-hand end 64 of the apparatus 50 in FIG. 1. The liquid biological sample is introduced (typically by means of a pipette) into the sample area 62 through the tower 52, which is referred to as the sample tower. The sample tower 52 has a sample port 66 at its upper end for admitting the sample into the apparatus 50, and an orifice 68 at its lower end which provides fluid communication with the sample area 62. To the right of the sample area 62 in FIG. 7, the channel 60 defines a decontamination zone 70 which constitutes a first portion of what may be referred to as a reaction area 72. The reaction area 72 occupies all of the volume of the channel 60 between the right-hand end of the sample area 62 and a vertical wall 74, and in the preferred embodiment has a length of approximately 0.93 inch and a volume of approximately 150 µL. The decontamination zone 70 occupies approximately half of the reaction area length (about 0.4 inch) and about half of its volume (about 65 µL). Contained within the decontamination zone 70 are the nucleic acid decontamination reagents 76 necessary for the decontamination reaction. The decontamination reagents 76 (the necessary active ingredients for the decontamination reaction as described above) may be those required for any suitable means of decontamination. The decontamination reagents 76 may be in any suitable form, including but not limited to a solid such as a dried film, lyophilized pellets or paper impregnated with the reagent. In the preferred embodiment of the invention, the decontamination reagents 76 are disposed upon and adhered to the upper interior surface of the channel 60 in dried form, at a location between the 0.60 and 0.80 inch points from the left-hand end of the base flange 58 in FIG. 7. The location of the dried decontamination reagents 76 can be seen in FIGS. 1, 2, 5, 6, 7 and 11. The preferred method for drying the decontamination reagents 76 is to dry the reagents in the presence of trehalose as taught in U.S. Pat. No. 4,891,319 and Patent Cooperation Treaty International Publication No. WO 87/00196, both owned by Quadrant Bioresources Limited and incorporated herein by reference. Briefly, the preferred drying technique protects biological materials against denaturation during drying and involves subjecting an aqueous system containing the biological material to a temperature above freezing in the presence of trehalose in an amount between about 0.05 and 20 weight percent based on the total weight of the aqueous system. Trehalose is a naturally occurring, non-reducing disaccharide also known as α-D-glucopyranosyl-α-D-glucopyranoside. The drying in the presence of trehalose may be simple air drying, preferably at atmospheric pressure. In the drying of the decontamination reagents 76 (and the amplification reagents to be described shortly), trehalose increases the chemical stability of the reagents significantly. Thus, the trehalose technology is an excellent system for drying any reagents to be used in the apparatus.

To the right of the decontamination zone 70 in FIG. 7, the channel 60 defines an amplification zone 78 which forms a second portion of the reaction area 72. In the preferred embodiment of the invention, the amplification zone 78 of the channel 60 is approximately 0.55 inch in length and has a volume of approximately 90 µL. Contained within the amplification zone 78 are the reagent or reagents 80 necessary for the amplification reaction. The amplification reagents 80 are those active agents required for any suitable nucleic acid amplification reaction, as described above. In a preferred embodiment of the present invention, the amplification method used is Strand Displacement Amplification. The amplification reagents 80, like the decontamination reagents 76, may be in any suitable form, including but not limited to a solid such as a dried film, lyophilized pellets, or paper impregnated with the reagents. The amplification reagents 80 may optionally include active agents such as a probe necessary for detection of the amplicon to be generated, as discussed above, particularly where detection is to be carried out in situ. Of course, the amplification reagents 80 need not be provided in the same form as the decontamination reagents 76, and may be contained in part in the decontamination reagents 76. In the preferred embodiment of the invention, the amplification reagent or reagents 80 are disposed upon and adhered to the upper interior surface of the channel 60, as illustrated in FIG. 7, in dried form. The preferred location for the amplification reagent or reagents 80 is between the 1.00 and 1.20 inch points measured from the left-hand end of the base flange 58 in FIG. 7. The trehalose technology preferred for drying of the decontamination reagents 76 is also preferred for drying of the amplification reagents 80.

Although it is preferred to provide the sample area 62 and reaction area 72 in the form of a continuous, undivided channel as shown, it is within the scope of the present invention to provide partitions or barriers between these areas if desired. It is also within the scope of the invention to provided partitions or barriers between the decontamination zone 70 and amplification zone 78 of the reaction area 72. Some or all of these portions or barriers (if provided) may comprise microchannels of the type described in copending U.S. patent application Ser. No. 08/213,304, or other types of flow control devices.

Figure 9:
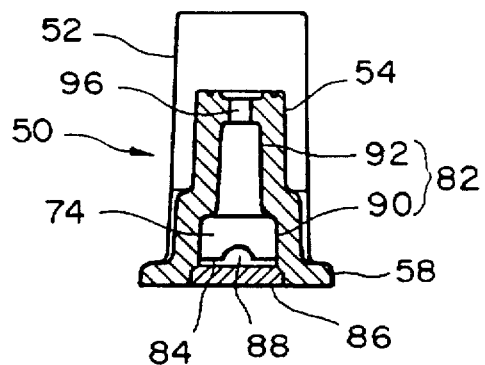
FIG. 9 is a sectional view taken along the line 9—9 in FIG. 7, illustrating the details of the pneumatic area.

The amplification zone 78 of the reaction area 72 communicates with a pneumatic chamber 82 by means of a microchannel 84 created by the virtual abutment of the wall 74 with the upper surface of a plug or insert 86 which forms the bottom wall of the channel 60. The gap between the wall 74 and the upper surface of the plug or insert 86, which creates the microchannel 84, is preferably about 0.006 inches in height and extends part way across the width of the channel 60 from either side thereof. However, as best seen in FIGS. 4, 6 and 9, the middle portion of the microchannel 84 is enlarged by means of a semicircular arch 88 formed in the wall 74 and having a radius of approximately 0.025 inch. The microchannel 84 serves as a liquid flow control means which substantially prevents the entry of the liquid biological sample into the pneumatic chamber 82, while permitting pneumatic communication with the channel 60 for the purpose of controlling the movement of the liquid biological sample therein. The sharp increase in height between the microchannel 84 and the adjacent area of the channel 60, combined with the wetting properties of the material of which the apparatus 50 is made, essentially prevents liquid flow due to capillary and hydrostatic forces. The microchannel 84 also reduces evaporative loss of the liquid biological sample through the pneumatic chamber 82. Addition of the semicircular arch or dome 88 to the microchannel 84 is advantageous in that it insures pneumatic communication between the reaction area 72 and the pneumatic chamber 82 in the event that the microchannel 84 becomes occluded as a result of condensation or during fabrication.

The details of the pneumatic chamber 82 may be best appreciated from FIGS. 2, 4, 7 and 9. In general, the pneumatic chamber 82 comprises a lower portion 90 and an upper portion 92, with the upper portion 92 being enclosed by the tower 54. The tower 54 is referred to herein as the pneumatic tower, and its purpose will be described shortly. The lower portion 90 of the pneumatic chamber 82 is approximately 0.13 inch in length, approximately 0.125 inch in width and approximately 0.85 inch in height, with the latter two dimensions being approximately the same as those of the channel 60. The lower portion 90 is bounded at one end by the straight wall 74 which defines the microchannel 84, and at the other end by the rounded right-hand end 94 of the apparatus 50, and thus has a truncated "U" shape when viewed in plan. Since the vertical walls of the apparatus 50 preferably have a slight inward taper of about 2° from bottom to top, the curved or rounded part of the lower portion 90 of the pneumatic chamber 72 has a slight frusto-conical shape. The upper portion 92 of the pneumatic chamber 82 is circular in cross-section when viewed in plan, again with a slight inward taper of about 2° from bottom to top to define a slightly frusto-conical shape. The upper portion 92 has a height of about 0.150 inch and varies in diameter from about 0.147 inch at the bottom to approximately 0.125 inch at the top. The top of the upper portion 92 of the pneumatic chamber communicates with the ambient atmosphere through a pneumatic port 96, which is cylindrical in shape and has a diameter of approximately 0.032 inch. As will be described in more detail below, the pneumatic port 96 allows the apparatus 50 to be connected to a pneumatic aspiration/dispensing means in order to control the flow of a liquid biological sample within the channel 60.

The volume of the pneumatic chamber 82, including the upper and lower portions 90 and 92, is approximately 35 µL. As in the case of the sample area 62 and the decontamination and amplification zones 70 and 78, respectively, of the reaction area 72, the volume and dimensions of the pneumatic chamber 82 may be varied in accordance with the requirements of particular applications.

Figure 10:
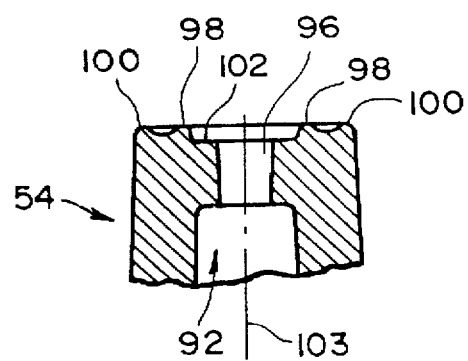
FIG. 10 is an enlarged sectional view through the upper portion of the pneumatic area in FIG. 9, illustrating the concentric sealing rings formed around the pneumatic port.

FIG. 10 is a detailed cross-sectional view of the upper portion of the pneumatic tower 54, illustrating a novel sealing arrangement which is provided around the pneumatic port 96. The sealing arrangement comprises a pair of rigid, concentric circular sealing rings 98 and 100 which surround the upper end of the pneumatic port 96. The sealing rings 98 and 100 are preferably integral with the pneumatic tower 54 and are made from the same material (preferably injection-molded polypropylene) as the remainder of the apparatus 50. As will be described in more detail hereinafter, the concentric sealing rings 98 and 100 serve to deform a resilient tip or collar carried by the pneumatic aspiration/dispensing means (not shown) when the latter is brought into contact with the top of the pneumatic tower 54. This creates an effective pneumatic seal around the pneumatic port 96, without requiring an "O" ring or other type of resilient sealing device to be provided on the apparatus 50 itself. This simplifies the design and construction of the apparatus 50 and reduces its cost. In a preferred embodiment, the concentric sealing rings 98 and 100 have a height of approximately 0.010 inch above the outlet plane 102 of the pneumatic port 96. The diameter of the sealing ring 98 is approximately 0.078 inch, and the diameter of the sealing ring 100 is approximately 0.182 inch, with both sealing rings being centered with respect to the axis 103 of the pneumatic port 96. The raised edge or rim of each sealing ring has a generally semicircular cross-section with a radius of approximately 0.005 inch, and the two sealing rings 98 and 100 are separated by an annular depression 104 which forms a smooth concave curve between the two raised sealing rings. The two sealing rings 98 and 100 may be replaced by a single sealing ring, if desired. However, the use of two concentric sealing rings 98 and 100 is preferred, since it improves the pneumatic seal between the pneumatic port 88 and the pneumatic aspiration/dispensing means, and also allows for some degree of misalignment between these two components without substantially affecting the integrity of the seal.

The details of the sample tower 52 may be appreciated from FIGS. 1-3, 7 and 8. The sample tower 52 has a generally raised or upstanding configuration, as shown, with a circular cross-section and outer walls that taper slightly inward (preferably at an angle of about 1°) from bottom to top to produce a frusto-conical shape. The interior walls 106 of the sample tower 52 taper in the opposite direction (i.e., inwardly from top to bottom, also at an angle of about 1°) between the sample port 66 and the orifice 68. Thus, the interior of the sample tower 52 has an inverted frusto-conical shape. This allows the sample tower 52 to function essentially as a funnel for directing the liquid biological sample (typically introduced through the sample port 66 by means of a pipette) to the orifice 68, which communicates with the sample area 62. The orifice 68 is circular in shape, matching the circular cross-section of the sample tower 52; however, for reasons to be discussed shortly, the diameter of the orifice 68 is smaller than the diameter of the adjoining parts of the sample area 62 and sample tower 52. In a preferred embodiment, the orifice 68 has a diameter of approximately 0.080 inch (slightly less than the interior height of the channel 60 and considerably less than its width), while the lower interior portion of the sample tower 52 has a diameter of approximately 0.11 inch. A 45° bevel 108 provides a smooth transition between the lower interior portion of the sample tower 52 and the orifice 98, and a similar 45° bevel 110 is formed at the top of the sample tower 52 to provide a smooth entry for a pipette into the sample port 66. The bevels 108 and 110, together with the inclined interior walls 106 of the sample tower 52, are useful in correcting for slight misalignments which may occur when a pipette is inserted into the sample tower 52 and through the orifice 68 in order to introduce or withdraw a liquid biological sample. The correction of such misalignments is particularly important when the pipette is being manipulated robotically, rather than manually, since a robotic manipulator is generally not capable of detecting and correcting for such misalignments on its own.

Figure 12:
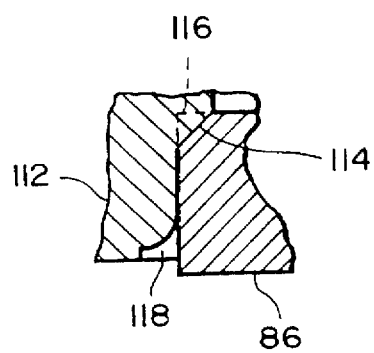
FIG. 12 is an enlarged sectional view through one bottom edge of the reaction area in FIG. 11, illustrating the manner in which the bottom plug or insert is received in the apparatus.

FIG. 6 illustrates the manner in which the apparatus 50 may be constructed. In general, the apparatus 50 comprises two parts, the first of which is a top portion 112 which includes the towers 52 and 54, the elongated rectangular body portion 56 and the base flange 58, and the second of which is the bottom plug or insert 86. Each of the parts 112 and 86 is made of an injection-molded plastic material, such as polypropylene, and the two parts are joined together by ultrasonic welding to form a single, unitary apparatus 50. The top portion 112 of the apparatus 50 has an opening 118 with a downwardly-facing 45° bevel 116. As illustrated in FIG. 12, the opening 118 curves outwardly at its lower extremity so that it is slightly larger than the plug or insert 86. This provides a smooth lead-in surface which assists in aligning the plug or insert 86 with the opening 118 prior to ultrasonic welding. The resulting gap between the edges of the plug or insert 86 and the perimeter of the opening 118 also prevents a ridge or protrusion of melted or softened plastic material from forming where these surfaces meet, as can sometimes occur during ultrasonic welding. The nature of the ultrasonic welding process is such that the weld will occur primarily between the bevel 116 and the sharp upper corner or edge 114 of the plug or insert 86. During welding, the plastic material of the top portion 112 and of the plug or insert 86 is momentarily melted at the junction between the corner 114 and bevel 116 and the boundary between them disappears. The plug or insert 86 is preferably made slightly thicker (by about 0.010 inch) than the corresponding opening 118 in the top portion 112 which receives it, as illustrated in FIG. 12, to insure that the bottom surface of the plug or insert 86 will always be the lowermost surface of the apparatus 50. When the apparatus 50 is placed on a heated platen, as will ordinarily occur when the apparatus 50 is used to carry out nucleic acid decontamination and amplification processes, this assures that the platen will be in good thermal contact with the plug or insert 86 so that heat can be efficiently transferred to the liquid biological sample contained within the channel 60.

As illustrated in FIG. 11, the upper corners 120 of the channel 60 that extend in the flow direction of the liquid biological sample are smoothly rounded, preferably at a radius of about 0.040 inch. This avoids sharp corners in the channel that would otherwise induce capillary flow of the liquid biological sample. As will be appreciated from the description that follows, the liquid biological sample fills the entire height of the channel 60 during the use of the apparatus 50 to carry out nucleic acid decontamination and amplification processes. Therefore, the configuration of the upper portion of the channel 60 has an important bearing on the performance of the apparatus. If desired, measures may also be taken to provide rounded corners along the lower edges of the channel 60, although this is somewhat more difficult given that the lower portion of the channel 60 is closed off by a separate plug or insert 86. Corners may be avoided altogether in the channel 60 by replacing the rectangular body portion 56 of the apparatus 50 with a one-piece cylindrical tube; however, while this method of construction is advantageous in reducing undesired capillary flow, it is more difficult to fabricate.

In the preferred embodiment of the apparatus 50 of FIGS. 1–12, the form factor of the channel 60 is chosen so that the trapping of air at the top of the reaction area 72 is reduced or eliminated, and so that the liquid biological sample develops a rectilinear profile which contributes to discrete, accurate and predictable positioning of the liquid bolus within the apparatus. In particular, the length of the decontamination zone 70 should be greater than the height of the channel 60, and the same should be true of the amplification zone 78. This form factor (i.e., length greater than height) ensures that air is not trapped at the top of the decontamination zone 70 or amplification zone 78, and therefore that the respective reagents 76 and 80 in these zones are fully exposed to the liquid biological sample.

The form factor of the channel 60 is also chosen so that evaporative loss of the liquid biological sample is minimized. This can be accomplished by choosing the channel dimensions such that the length of the liquid bolus is substantially greater than its width or height, so that only a relatively small frontal area at either end of the bolus is exposed to air. In the preferred embodiment of the invention, the length of a 55 µL liquid bolus in a channel 60 having a width of approximately 0.125 inch and a height of approximately 0.085 inch is about 0.34 inch. In general, a ratio of at least about 2:1 should be maintained between the length of the liquid bolus and the largest transverse dimension of the channel 60. This will generally result in a channel 60 whose length is much greater than its width or height, although practical considerations may limit the length and narrowness of the channel 60.

The apparatus 50 may be conveniently constructed of any suitable plastic and by any suitable plastic processing method, either as a single part or as multiple parts for subsequent assembly. Such materials and methods include, but are not limited to, thermoplastic polymers molded using conventional molding techniques such as injection molding. Exemplary thermoplastic polymers include polypropylenes, polymethylpentene, and copolymers and mixtures thereof.

As described earlier, the apparatus 50 is preferably produced from polypropylene plastic that is injection molded to form two parts, indicated at 112 and 86 in FIG. 6. The top part 112 is inverted and the reagents 76 and 80 necessary for decontamination and amplification are dried as films onto the inner top surface of the decontamination zone 70 and amplification zone 78, respectively, in the channel 60. Subsequently, the bottom plug or insert 86 is ultrasonically welded onto the top part 112, as described above, to form a single unit 50.

In the apparatus 50, the liquid biological sample is confined in the decontamination and amplification zones 70 and 78, respectively, of the reaction area 72 in a manner such that there is preferably no head space. Head space refers to the space filled with air above a liquid in a container. Head space is often not desirable in systems that require a liquid to undergo a chemical reaction at a uniform temperature, since the head space allows a portion of the liquid to condense on the walls and top of the container and to exist at a different temperature than the bulk of the liquid. By being at a different temperature, some chemical reactions are not completed properly. In the case of the amplification of a liquid sample, this usually means that reduced amplification is obtained. In the apparatus 50, the liquid biological sample fully contacts the top of the decontamination zone 70 and amplification zone 78, with virtually no head space.

When used for the performance of biological processes including an amplification step, one of the primary functions of the apparatus 50 is to provide an environment which is free of contaminating amplicons. In addition to liquid nucleic acid samples that contain contaminating nucleic acids, contact of a sample with contaminated items is a major mode of amplicon contamination. In a laboratory that is performing nucleic acid amplification, everything is a potential source of amplicon contamination. The apparatus 50 physically isolates the amplification environment within the amplification zone 78. The design of the apparatus 50 includes no moving parts that could be opened at any time, and therefore never exposes the amplification zone 78 to the amplicon-contaminated external environment. Internal contact of the sample within the amplification zone 78 is prevented by the decontamination zone 70 and the pneumatic chamber 72 on either side, and by the microchannel 84.

The air flow through the apparatus 50 is designed to minimize aerosol amplicon contamination caused by the pipette of the pneumatic aspiration/dispensing means, which is coupled to the pneumatic port 96. During the various stages before amplification, the pipette only withdraws air from the apparatus 50, but does not dispense air into the apparatus. In this way, amplicons which may be contaminating the pipette are drawn away from the amplification zone 78.

Once amplification has occurred, the direction of air flow is reversed. Now the pipette of the pneumatic aspiration/dispensing means only dispenses air into the apparatus 50. In this way, amplicons in the amplification zone 78 flow away from the pipette, reducing the possibility of aerosol amplicon contamination of the pipette. The amplified liquid sample is returned to the sample area 62 of the apparatus 50 and can be removed for subsequent nucleic acid probe assay.

The size and physical configuration of the apparatus 50 allow an array of similar apparatus to be reacted simultaneously, and their final amplified output to be automatically transferred to a nucleic acid probe assay without operator intervention.

Figure 13:
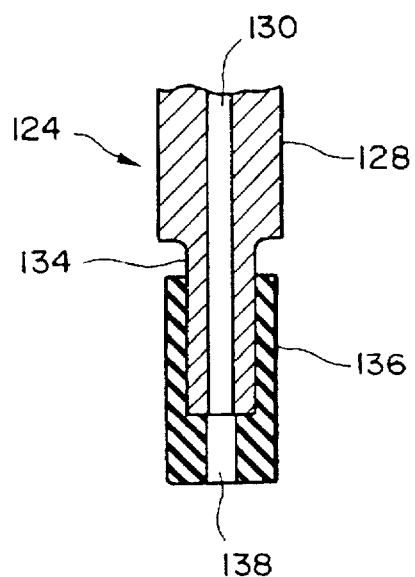
FIGS. 13 and 14 are sectional and exploded views, respectively, of a portion of the pneumatic aspiration/dispensing means which is used to control the flow of a liquid biological sample within the apparatus of FIGS. 1–12.
Figure 14:
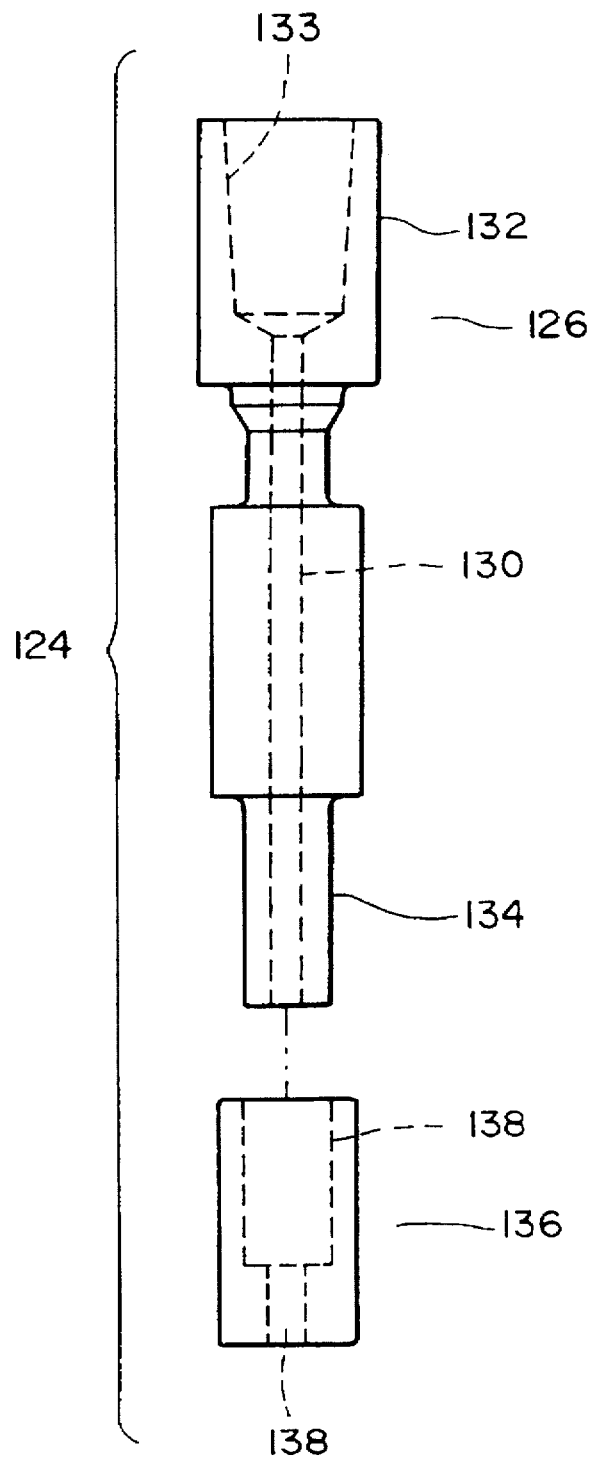
Figure 23:
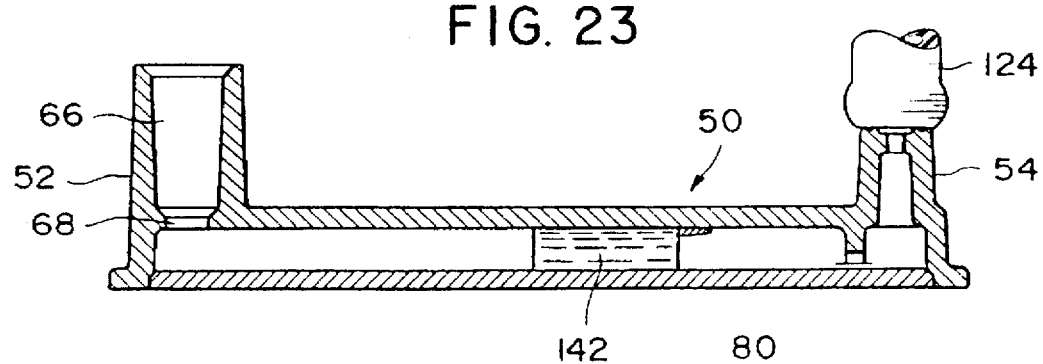
Figure 24:
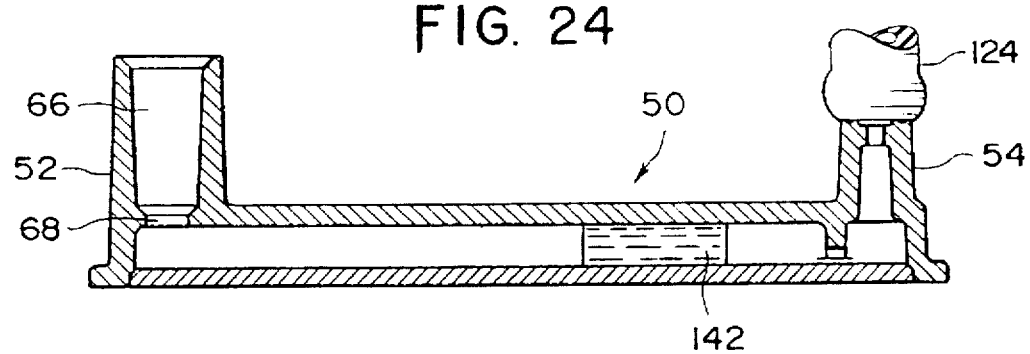

FIGS. 13 and 14 illustrate a preferred type of pneumatic aspiration/dispensing means 124 which may be used to control the movement of a liquid biological sample within the apparatus of FIGS. 1–12. The pneumatic aspiration/dispensing means 124 includes a rigid, generally cylindrical pipette 126 made of plastic. An axial conduit or lumen 130 extends vertically through the pipette 126 for dispensing or aspirating air. It will be understood that the upper portion 132 of the pipette 126 in FIG. 14 is connected to a source of positive and negative air pressure (not shown) and, optionally, to a robotic manipulator (also not shown) which is programmed to bring the pneumatic aspiration/dispensing means 124 into contact with the pneumatic towers 54 of one or several apparatus 50. To this end, the upper portion 132 of the pipette 124 is formed with an enlarged cylindrical cavity 133 whose interior walls taper slightly inward from top to bottom, and whose bottom portion communicates with the lumen 130. The cavity 133 allows the pipette 126 to be frictionally coupled to the aspiration/dispensing nozzle of a robotic manipulator, as described on the aforementioned U.S. patent application of Allen S. Reichler et al, Ser. No. 08/409,821 filed on even date herewith and entitled "System for Nucleic Acid Based Diagnostic Assay". The lower portion 134 of the pipette 126, which may have a reduced diameter as shown, carries a resilient tip 136 which is preferably made of silicone rubber. The resilient tip 136 is generally cylindrical in shape, with an outside diameter of about 0.190 inch and an internal cylindrical cavity 138 conforming to the size and shape of the lower portion of the pipette 134. In the assembled condition of the pneumatic dispensing/aspiration means 124, the resilient tip 136 fits tightly around the lower portion 134 of the pipette 126. A cylindrical hole 138 having a diameter of about 0.050 inch is formed through the lower end of the resilient tip 136 and communicates with the lumen 130 of the pipette 126, which has a similar diameter. In use, the assembled pneumatic aspiration/dispensing means 124 is lowered (manually or robotically) to bring the resilient tip 136 into contact with the upper end of the pneumatic tower 54 of the apparatus 50, such that the hole 138 in the resilient tip 136 aligns with the pneumatic port 96. By exerting slight pressure between the resilient tip 136 and the pneumatic tower 54, the concentric sealing rings 98 and 100 surrounding the pneumatic port 96 are caused to bear against and slightly deform the resilient tip 136. This creates an effective pneumatic seal around the interface between the hole 138 and the pneumatic port 96. Pneumatic aspiration and dispensing can then be carried out by the positive and negative air pressure source (not shown) attached to the apparatus 124. A programmable robotic aspiration/dispensing system, such as the TECAN RSP 9000 Series manufactured by TECAN AG of Hombrechtiken, Switzerland, may be fitted with the pipette 126 and resilient tip 136 of FIGS. 13 and 14, and the resulting arrangement may be used to control the movement of a liquid biological sample in the apparatus 50 of FIGS. 1–12.

The manner in which the flow or movement of a liquid nucleic acid sample within the apparatus 50 of FIGS. 1–12 is controlled using the pneumatic aspiration/dispensing means 124 of FIGS. 13 and 14 is illustrated in the sequence views of FIGS. 15–31.

FIG. 15 shows the initial empty state of the apparatus 50. A pipette tip 140 has been lowered, either manually or robotically, into the sample tower 52 and part way into the sample area 62 via the orifice 68, in order to introduce a liquid biological sample into the sample area 62. Although the apparatus 50 will normally be positioned between a pair of heating platens as disclosed in copending application Ser. No. 08/409,821, the heating platens have been deleted in FIG. 15 (and in the remaining sequence views) for clarity.

FIG. 16 shows the liquid sample 142 in the sample area 62. It will be observed that, as a consequence of the dimensions of the apparatus 50, the surface tension of the liquid sample 142 and the wettability of the plastic material of which the apparatus 50 is made, the liquid sample 142 is in the form of a bolus with a distinct right-hand surface 143. As a result, the bolus remains within the sample area 62 despite the absence of a partition between the sample area 62 and the reaction area 72.

FIG. 17 shows the resilient tip 136 of the pneumatic aspiration/dispensing means 124 engaged with (and slightly deformed by) the pneumatic tower 54 of the apparatus 50. Air is being withdrawn from the apparatus 50 by the pneumatic aspiration/dispensing means 124 through the pneumatic port 96 and, as a result, the liquid sample 142 is being moved into the decontamination zone 70 of the reaction area 72.

FIG. 18 shows the liquid sample 142 being aspirated still further into the decontamination zone 70 of the reaction area 72. As the liquid bolus enters the decontamination zone 70, it is brought into contact with the decontamination reagents 76.

FIG. 19 shows the liquid sample 142 fully positioned within the decontamination zone 70. The decontamination reagents 76 are completely contacted (covered) by the liquid bolus 142, and the liquid bolus retains its rectilinear edges.

FIG. 20 shows the liquid sample 142 during decontamination. The pneumatic aspiration/dispensing means 124 has been disengaged from the apparatus 50 and is not needed until decontamination is completed and movement of the liquid sample 142 to the next area is required. Alternatively, the pneumatic aspiration/dispensing means 124 need not be disengaged, provided that aspiration does not take place until decontamination is completed.

FIGS. 21-24 show the return of the pneumatic aspiration/dispensing means 124 into engagement with the pneumatic port 96 of the apparatus 50, and the movement of the liquid sample 142 from the decontamination zone 70 into the amplification zone 78. This is achieved by using the pneumatic aspiration/dispensing means 124 to aspirate air from the apparatus 50 through the pneumatic port 96.

Figure 25:
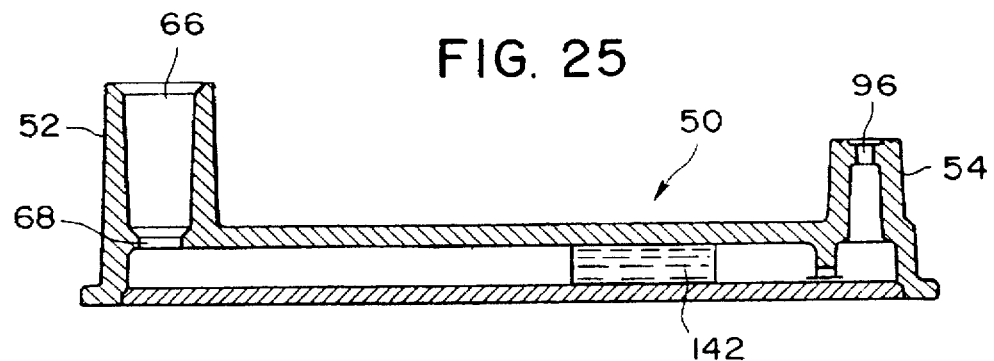
Figure 26:
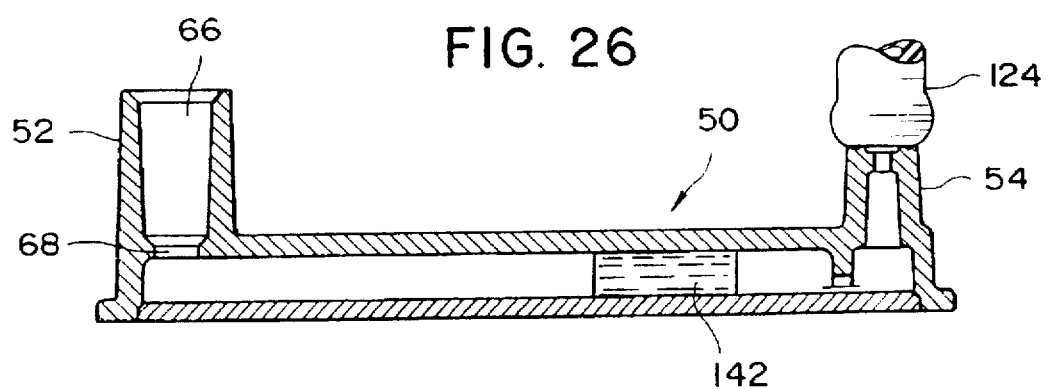
Figure 27:
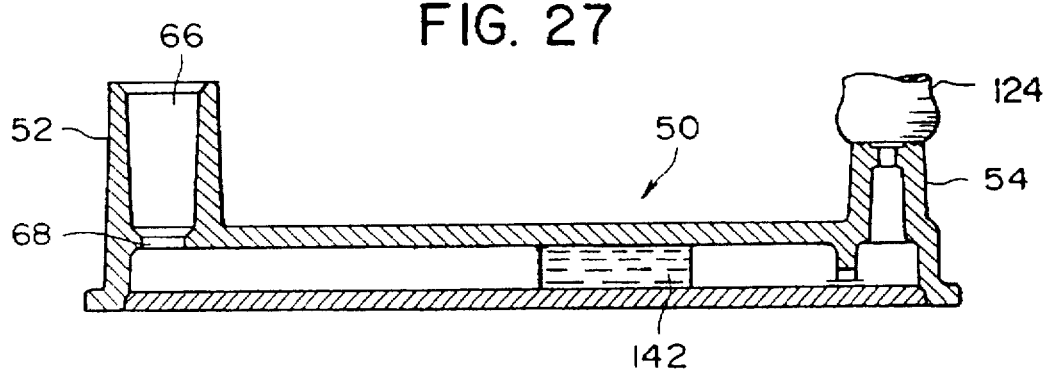
Figure 28:
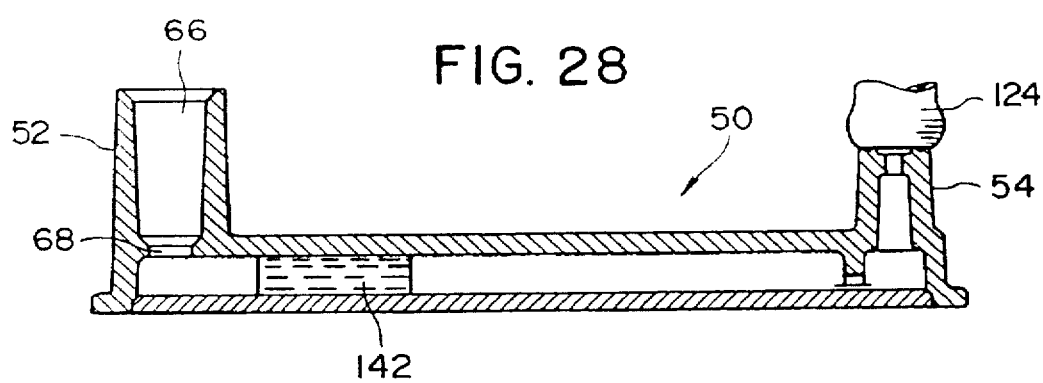

FIG. 25 shows the liquid bolus 142 during amplification. Again, the pneumatic aspiration/dispensing means 124 has been disengaged from the pneumatic port 96 of the apparatus 50, and is not needed until the amplification is completed and movement of the liquid sample 142 is required. However, as with the decontamination step, the pneumatic aspiration/dispensing means 124 need not be disengaged provided that pneumatic dispensing does not take place until amplification is completed.

FIGS. 26-29 show the return of the pneumatic aspiration/dispensing means 124 into engagement with pneumatic port 96 of the apparatus 50, and the reversal of the movement of the liquid sample 142 back through the decontamination zone 70 to the sample area 62. The reversal of flow is achieved through the dispensing of air by the pneumatic aspiration/dispensing means 124 into the apparatus 50 via the pneumatic port 96. In the preferred embodiment, in order to move the amplified sample 142 all the way back to the sample area 62, the pneumatic aspiration/dispensing means 124 would dispense a volume of air equal to or greater than the total volume of the decontamination zone 70 and the sample area 62 combined, or, in the embodiment specifically disclosed, a volume of air greater than or equal to about 125 µL.

Figure 29:
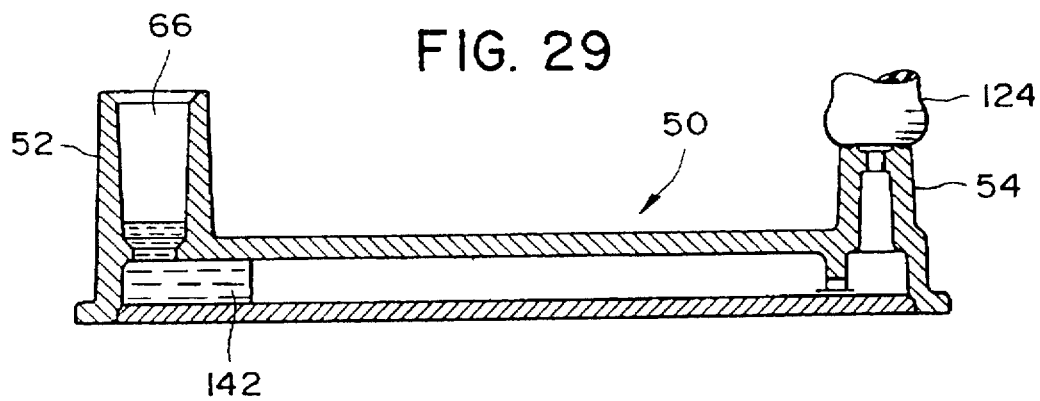

It will be noted from FIG. 29 that the liquid biological sample 142 is returned to the sample area 62 by the pneumatic aspiration/dispensing means 124 in such a manner that one end of the bolus is forced through the restricted orifice 68 and resides just above the bottom of the sample tower 52. In this position, the restricted orifice 68 exerts a capillary holding force on the bolus 142, counteracting the natural tendency of the bolus to move back toward the decontamination zone 70 of the reaction area 72 under the influence of capillary forces and gravity. In this way, the liquid sample 142 may be held in the sample area 62 until such time as it can be removed from the apparatus 50 for assay. In addition to maintaining the position of the liquid sample 142 in the sample area 62, the restricted orifice 68 is also advantageous in that it allows the upper surface of the bolus 142 to be elevated somewhat for more convenient removal by a pipette or the like.

The physical mechanism by which the restricted orifice 68 exerts a holding force on the bolus 142 may be explained as follows. The difference in pressure between a liquid and the ambient air may be expressed by the relationship $\Delta P = 2\tau/R$, where x is the surface tension of the liquid, R is the effective radius of the opening through which the liquid is exposed to air, and $\Delta P$ is the maximum pressure difference created by surface tension effects. Because the restricted orifice 68 has a smaller radius than the effective radius of the channel 60, it exerts an upward pressure on the bolus that is greater than the downward pressure exerted by the end of the bolus in the sample area 62.

Figure 30:
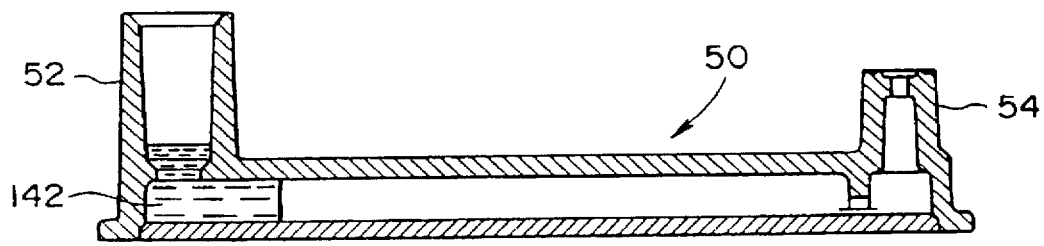
Figure 31:
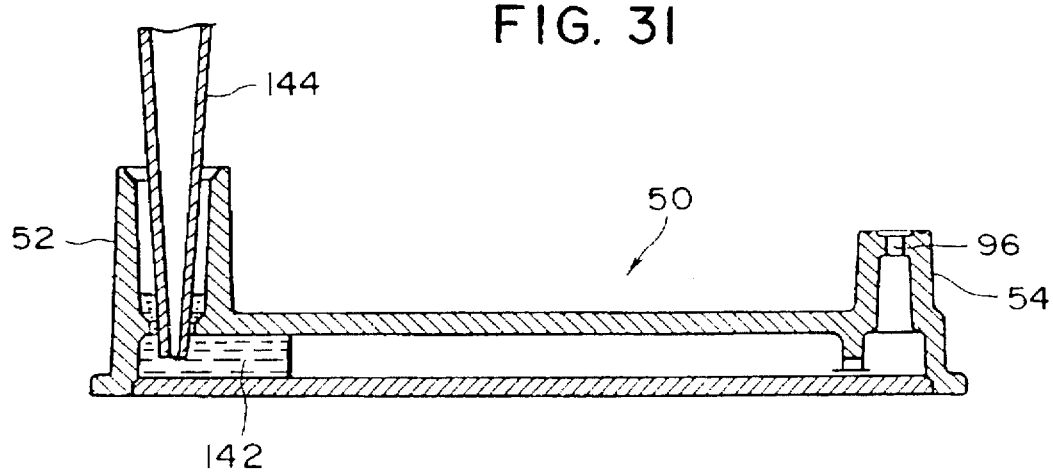

FIGS. 30 and 31 illustrate the condition of the apparatus 50 after the liquid biological sample 142 has been returned to the sample area 62 and the pneumatic aspiration/dispensing means 124 has been removed from the pneumatic port 96. The surface of the liquid bolus 142 is located at the bottom of the sample tower 52, just above the orifice 68. A pipette 144 is lowered through the sample tower 52 and orifice 68 so that it extends part way into the sample area 62, and is used to aspirate the sample from the apparatus 50. The pipette 144 (like the pipette 140 of FIG. 15) can be of the disposable type and can be controlled manually or automatically, in the latter case by a conventional robotic apparatus of the type described earlier. During the interval after the sample 142 has been returned to the sample area 62 but before it has been recovered by the pipette 144, the liquid bolus 142 is held in place by the restricted orifice 68, which counteracts the tendency of the bolus to flow by capillary action in the direction of the decontamination zone 70 of the reaction area 72. This is an important advantage in situations where, for example, a number of different apparatus 50 are being processed automatically by a single robotic manipulator. Under those circumstances, an interval of several minutes or more may elapse between the time when the liquid bolus 142 is returned to the sample area 62 of a given apparatus 50 by the pneumatic aspiration/dispensing means 124, and the time when the same sample 142 is recovered by the pipette 144.

During the sequence of operations represented by FIGS. 15-31, the sample tower 52 performs an important function in that it reduces evaporative loss of the sample 142. As described earlier, evaporative loss of the sample can be a significant problem given the relatively small volume of liquid involved (approximately 55 µL), the temperatures to which it is subjected (up to 80° C.) and the amount of time required for the decontamination and amplification processes to take place (approximately 1 and 2 hours, respectively). In the absence of the sample tower 52, significant evaporative loss can occur through the sample area 62 and orifice 68. However, liquid vapors that are produced by the sample 142 during decontamination and amplification tend to concentrate within the sample tower 52 before escaping to the ambient atmosphere, thereby producing a humidity gradient that reduces the rate of evaporative loss from the sample area 62 and orifice 68. This effect can be maximized by maximizing the length of the path along which the gradient forms (the height of the sample tower 52) and minimizing the cross-sectional area transverse to the gradient direction (the internal cross-sectional area of the sample tower 52). The sample tower also acts as a shroud for the orifice 68, restricting air circulation in the vicinity of the orifice 68. Finally, the interior walls 106 of the sample tower 52 act as a condensation surface for vapors produced by the sample 142, since the sample tower 52 is relatively far from the heating platens that are used to incubate the liquid sample in the body portion 56 of the apparatus 50. The condensed sample vapor that deposits on the interior walls 106 of the sample tower 52 is returned to the sample area 62 through the orifice 68 in the form of droplets, and is recovered along with the remainder of the liquid sample 142 by the pipette 144 of FIG. 31.

Figure 32:
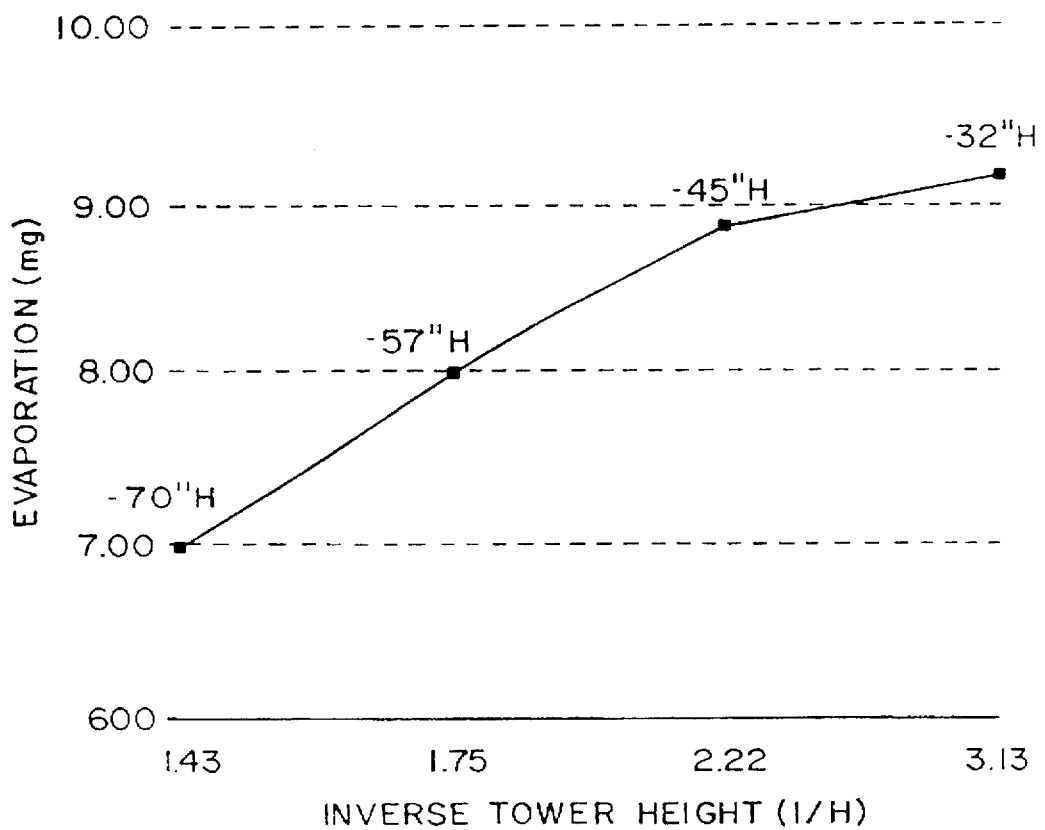
FIG. 32 is a graph illustrating the relationship between sample tower height and evaporative loss in the apparatus of FIGS. 1–12.

FIG. 32 is a graph which shows the relationship between evaporative loss and sample tower height for a given sample tower radius. The graph shows that evaporative loss decreases significantly with increasing sample tower height. A sample tower height of 0.45 inch was chosen for the preferred embodiment of the present invention due to the constraints imposed by other equipment in which the apparatus 50 is placed after nucleic acid amplification, but it will be evident that further increases in the sample tower height will cause a still further decreases in evaporative loss.

In alternative embodiments of the invention, structures other than (or in addition to) the sample tower 52 may be used to reduce evaporative loss. These include pierecable septa, perforated membranes, and robotically displaceable covers or lids. All of these alternative structures are effective in reducing evaporative loss, but allow sufficient air passage to enable controlled movement of the liquid bolus using a pneumatic aspiration/dispensing means.

The pneumatic tower 54 at the opposite end of the apparatus performs a function similar to that of the sample tower 52. By lengthening the pneumatic chamber 82, the pneumatic tower 54 provides a humidity gradient that reduces evaporative loss through the pneumatic port 96, and relatively cool condensation surfaces that reduce evaporative loss still further by returning the condensate to the amplification zone 78. In addition, the relatively small diameter of the pneumatic port 96 offers an additional barrier against evaporative losses.

During use of the apparatus 50, heating platens are positioned above and below the body portion 56 so that they cover the decontamination and amplification zones 70 and 78 of the reaction area 72, but do not cover the sample area 62. As a result, when the heating platens are energized to apply heat to the reaction area 72 at various times during the sequence of operations represented by FIGS. 15–31, the walls of the sample area 62 remain somewhat cooler than the walls of the reaction area 72 and serve as condensation surfaces for vapor produced by the liquid sample 142 during heating. This vapor is produced primarily during the decontamination and amplification steps of FIGS. 20 and 25, respectively, when the platens are applying heat to the sample 142. The condensed droplets which form on the walls of the sample area 62 during these intervals are then recovered when the sample 142 moves back into the sample area 62, as shown in FIGS. 26–31. This condensate recovery phenomenon further reduces evaporative loss of the liquid sample 142 from the apparatus 50.

In general, the liquid sample employed in the present invention will be an aqueous preparation containing the target nucleic acid (i.e., ribonucleic acid (RNA) or deoxyribonucleic acid (DNA)) and any contaminating amplicons, with either (or both) the target nucleic acid and the amplicons in single-stranded form. For example, the target nucleic acid may comprise randomly sheared genomic DNA fragments. The preparation will be in a form suitable for use in a nucleic acid amplification procedure, in accordance with known techniques. Target nucleic acid will typically comprise nucleic acid fragments of from about 5,000 nucleotides in length to about 200,000 nucleotides in length (with lengths representing an average of the lengths found in the preparation). Within the target nucleic acid is the sequence of interest to be amplified. The sequences for amplification can range from as few as ten base pairs to several thousand, with base pairs of about 15 to about 200 preferred.

The length of amplicons to be degraded by the method of the present invention will vary depending upon the particular nucleic acid amplification method by which the amplicons are produced, but will usually be at least about 25 nucleotides in length, and typically will be not more than about 2,000 nucleotides in length. When the amplicons are produced by Strand Displacement Amplification (SDA), they will typically be not more than about 1200 nucleotides in length.

Decontamination to remove contaminating amplicons in a sample containing target nucleic acid sequence may be carried out by any suitable means, including using double strand specific exonucleases and single strand of specific exonucleases. Hence, decontamination reagents may contain one or more single strand or double strand specific exonuclease. For example, R. Griffis, PCT Application WO 91/00363 (published 10 Jan. 1991) discloses a method of decontaminating a PCR reaction product with a 5' lambda exonuclease. Similarly, Y. S. Zhu et al, *Nucleic/Acids Res.* 19, 2511 (1991), disclose the use of exonuclease III for removing amplicons from a PCR reaction product. Both the lambda exonuclease and exonuclease III are double-strand specific exonucleases. Any single strand-specific exonuclease can be employed in carrying out the present invention so long as it is capable of degrading the amplicons. Examples of suitable single-strand specific exonucleases include, but are not limited to, exonuclease VII (see, e.g., J. Chase and C. Richardson, *J. Biol. Chem.* 249, 4545–4552 (1974); J. Chase and C. Richardson, *J. Biol. Chem.* 249, 4553–4561 (1974)), exonuclease I (see, e.g., R. Brody, *Biochemistry* 30 7072–7080 (1991)), Pfu DNA polymerase from *Pyrococcus furiosus* (Stratagene, Lajolla, Calif.), DNA polymerase, T4 DNA polymerase, spleen exonuclease (*J. Biol. Chem.* 253; 424 (1978)), T5 D15 Exonuclease (*Nucleic/Acids Research* 19, 4127 (1991)), "Vent" DNA polymerases from *Thermocuccus litoralis* (New England Bilabs, Beverly, Mass.), and DNA polymerases which have 3'-5' exonuclease activity. DNA polymerases having 3'-5' exonuclease activity employed in carrying out the invention should be capable of degrading phosphorothioate linkages if the amplicons to be degraded are the products of SDA. See generally, F. Eckstein, *Ann. Rev. Biochem.* 54, 367–402 (1985) (3'–5' exonuclease activity of T4 DNA polymerase can cleave phosphorothioate DNA but that from *E. coli* DNA polymerase I cannot). It will be appreciated that the exonuclease need only degrade the amplicons sufficiently so that the amplicons will not serve as a substrate for a subsequent nucleic acid amplification reaction (i.e., produce a false positive result from a nucleic acid preparation which would not otherwise serve as a substrate for the amplification reaction for contamination by the amplicons).

Alternatively, the decontamination step of the process may be performed using the techniques taught in U.S. Pat. No. 5,035,996 or published European Patent Application No. 0 415 755 A2, both of which are incorporated herein by reference. These patent publications are owned by Life Technologies Inc. and describe decontamination techniques wherein one of the four normal ribonucleotides or deoxyribonucleotides used in the amplification procedure is replaced with an exo-sample nucleotide. Then, after amplification, any amplicons which may contaminate another sample are subjected to a physical, chemical, enzymatic, or biological treatment to render the amplicons containing the exo-sample nucleotide substantially unamplifiable. A preferred exo-sample nucleotide is deoxyuridine (dUTP) when the target nucleic acid is DNA. When dUTP is utilized as the exo-sample nucleotide, the contaminating amplicons are subjected to enzymatic treatment with uracil DNA glycosylase (UDG) to render the amplicons unamplifiable.

Amplification of a selected, or target, nucleic acid sequence may be carried out by any suitable means. See generally D. Kwoh and T. Kwoh, *Am. Biotechnol. Lab.* 8, 14–25 (1990). Examples of suitable amplification techniques include, but are not limited to, polymerase chain reaction (PCR), ligase chain reaction (LCR), Strand Displacement Amplification (SDA), transcription-based amplification (see D. Kwoh et al, *Proc. Natl. Acad Sci. USA* 86, 1173–1177 (1989)), self-sustained sequence replication (or "3SR") (see J. Guatelli et al, *Proc. Natl. Acad Sci. USA* 87, 1874–1878 (1990)), the Qβ replicase system (see P. Lizardi et al. *Bio Technology* 6, 1197–1202 (1988)), nucleic acid sequence-based amplification (or "NASBA") (see R. Lewis, *Genetic Engineering News* 12 (9), 1 (1992)), the repair chain reaction (or "RCR") (see R. Lewis, supra), and boomerang DNA amplification (or "BDA") (see R. Lewis supra). Strand Displacement Amplification (or "SDA"), is preferred.

Strand Displacement Amplification may be carried out in accordance with known techniques. See generally G. Walker et al, *Proc. Natl. Acad. Sci. USA* 89, 392–396 (1992); G. Walker et al, *Nucleic Acids Res.* 20, 1691–1696 (1992). For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence which hybridizes to the target sequence to be amplified and/or detected. The flanking sequence, which serves to facilitate binding of the restriction enzyme to the recognition site and provides a DNA polymerase priming site after the restriction site has been nicked, is preferably about 15 to 20 nucleotides in length; the restriction site is functional in the SDA reaction (i.e., phosphorothioate linkages incorporated into the primer strand do not inhibit subsequent nicking— a condition which may be satisfied through use of a nonpalindromic recognition site); the oligonucleotide probe portion is preferably about 13 to 15 nucleotides in length.

SDA is carried out with a single amplification primer as follows: a restriction fragment (preferably about 50 to 100 nucleotides in length and preferably of low GC content) containing the sequence to be detected in prepared by digesting a DNA sample with one or more restriction enzymes, the SDA amplification primer is added to a reaction mixture containing the restriction fragment so that a duplex between the restriction fragment and the amplification primer is formed with a 5' overhang at each end, a restriction enzyme which binds to the restriction site on the amplification probe (e.g., HincII) is added to the reaction mixture, an exonuclease deficient DNA polymerase (e.g., an exonuclease deficient form of *E. coli* DNA polymerase I, see V. Derbyshire, *Science* 240, 199–201 (1988)) is added to the reaction mixture, and three dNTPs and one dNTP[S], with the dNTP[S] selected so that a phosphorothioate linkage is incorporated into the primer strand at the restriction site for the particular restriction enzyme employed (e.g., dGTP, dCTP, dTTP, and dATP[S] when the restriction enzyme is HincII are added to the reaction mixture. The DNA polymerase extends the 3' ends of the duplex with the dNTPs to form a downstream complement of the target strand. The restriction enzyme nicks the restriction site on the amplification primer, and the DNA polymerase extends the 3' end of the amplification primer at the nick to displace the previously formed downstream complement of the target strand. The process is inherently repetitive because the restriction enzyme continuously nicks new complementary strands as they are formed form the restriction site, and the DNA polymerase continuously forms new complementary strands from the nicked restriction site.

SDA can also be carried out with a pair of primers on a double stranded target DNA sequence, with the second primer binding to the 3' end of the complementary strand, so that two sets of repetitive reactions are occurring simultaneously, with the process proceeding exponentially because the products of one set of reactions serve as a target for the amplification primer in the other set of reactions.

The step of first digesting the DNA sample to form a restriction fragment in a SDA reaction can be eliminated by exploiting the strand displacing activity of the DNA polymerase and adding a pair of "bumper" primers which bind to the substrate at a flanking position 5' to the position at which each amplification primer binds. Each bumper primer extension product displaces the corresponding amplification primer extension product. Amplification primers, which are present in excess, then bind to the displaced primer extension products, and upon extension, a double-stranded DNA fragment is formed which can then serve as a substrate for exponential SDA with that pair of amplification primers.

Polymerase chain reaction (PCR) may also be carried out in accordance with known techniques. See, e.g., U.S. Pat. Nos. 4,683,195; 4,683,202; 4,800,159; and 4,965,188 (the disclosure of all U.S. Patent references cited herein are to be incorporated herein by reference). In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extensions product of the other primer, and then heating the sample to separate the primer extension products from their templates if the sequence or sequences to be detected are present. These steps are continued cyclically, preferably in a thermal cycler, until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques.

Ligase chain reaction (LCR) is also carried out in accordance with known techniques. See, e.g., R. Weiss, *Science* 254, 1292 (1991). In general, the reaction is carried out with two pairs of oligonucleotide probes; one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

The foregoing is illustrative of the present invention, and is not to be construed as limiting thereof, as numerous alternatives to those methods and devices described above which incorporate the present invention will be apparent to those skilled in the art. The invention is accordingly defined by the following claims, with equivalents of the claims to be included therein.

What is claimed is:

1. An apparatus for containing a liquid biological sample and for performing a biological process thereon, comprising:

a sample area for receiving a liquid biological sample, said sample area having an orifice for admitting said sample into said sample area;

at least one reaction area in fluid communication with said sample area;

a pneumatic area in pneumatic communication with said reaction area and said sample area;

a pneumatic port in said pneumatic area for connection of said apparatus to a pneumatic aspiration/dispensing means, said aspiration/dispensing means causing the flow of said liquid biological sample between said sample area and said reaction area; and a sample tower located above said sample area and in fluid communication with said sample area through said orifice for reducing evaporative loss of said liquid biological sample from said sample area and said reaction area, said sample tower having a sample port at an upper end thereof for admitting said liquid biological sample into said sample area through said orifice, said sample tower having said orifice at a lower end thereof;

wherein said orifice is of smaller size than the adjacent portion of said sample area to provide a capillary lock for inhibiting capillary flow of said liquid biological sample from said sample area to said reaction area;

wherein said pneumatic area includes a pneumatic tower for reducing evaporative loss of said liquid biological sample through said pneumatic area, said pneumatic tower having said pneumatic port at an upper end thereof, and wherein said pneumatic port is encircled by a pair of rigid, concentric sealing rings adapted to make sealing contact with a resilient portion of said pneumatic aspiration/dispensing means.

2. The apparatus of claim 1, wherein said sample tower has interior walls tapering inwardly in the direction from said sample port to said orifice.

3. The apparatus of claim 1, wherein said sample tower, said sample port and said orifice are each circular in cross-section.

4. The apparatus of claim 1, wherein said sample area and said reaction area are provided in the form of a continuous channel through which said liquid biological sample flows in the form of a liquid bolus.

5. The apparatus of claim 1, wherein said apparatus is elongate in shape with said sample area and said pneumatic area at opposite ends thereof, and said reaction area positioned therebetween.

6. The apparatus of claim 1, further comprising a microchannel positioned between said reaction area and said pneumatic area for substantially preventing liquid flow by hydrostatic force therethrough.

7. The apparatus of claim 6, wherein said apparatus is devoid of liquid flow control means between said orifice and said microchannel.

8. The apparatus of claim 6, wherein said microchannel has an enlarged opening extending partially across said microchannel.

9. The apparatus of claim 1, wherein said apparatus is formed from non-wettable material to substantially prevent liquid flow by capillary action.

10. The apparatus of claim 9, wherein said apparatus is formed from polypropylene.

11. The apparatus of claim 1, wherein at least a first dried reagent necessary for said biological process is affixed to an internal surface of said reaction area.

12. The apparatus of claim 11, wherein a second dried reagent necessary for said biological process is affixed to an internal surface of said reaction chamber at a location different from that of said first dried reagent.

13. The apparatus of claim 12, wherein said biological process has a decontamination step utilizing said first dried reagent and a nucleic acid amplification step utilizing said second dried reagent, and wherein the locations of said first and second dried reagents in said reaction chamber are such that said liquid biological sample is subjected to said decontamination step prior to said amplification step.

14. A system for performing a biological process, comprising:

an apparatus for containing a liquid biological sample, said apparatus including a sample area for receiving said liquid biological sample, at least one reaction area in fluid communication with said sample area, a pneumatic area in pneumatic communication with said reaction area and said sample area, and a pneumatic port in said pneumatic area; and pneumatic aspiration/dispensing means adapted to be brought into contact with said pneumatic port to cause said liquid biological sample to flow between said sample area and said reaction area;

wherein said pneumatic port of said apparatus is encircled by at least one rigid sealing ring and said pneumatic aspiration/dispensing means has a resilient portion adapted to be deformed by contact with said sealing ring to create a pneumatic seal around said pneumatic port.

15. The system of claim 14, wherein said pneumatic aspiration/dispensing means comprises a rigid aspiration/dispensing pipette and said resilient portion comprises a resilient tip affixed to said pipette, said resilient tip having an opening therein communicating with the lumen of said pipette and with the pneumatic port of said apparatus.

16. The system of claim 15, wherein said resilient tip is made of silicone rubber.

17. The system of claim 15, wherein said sealing ring is one of a pair of rigid, concentric sealing rings encircling said pneumatic port and adapted to be brought into contact with said resilient tip.

* * * * *